United States Patent
Homan et al.

(10) Patent No.: US 7,938,771 B2
(45) Date of Patent: May 10, 2011

(54) ENDOSCOPE IMAGE PICK-UP APPARATUS

(75) Inventors: Masatoshi Homan, Hino (JP); Kaoru Kotouda, Hachioji (JP); Motoo Azuma, Tokorozawa (JP)

(73) Assignee: Olympus Corporation, Tokyo (JP)

( * ) Notice: Subject to any disclaimer, the term of this patent is extended or adjusted under 35 U.S.C. 154(b) by 1109 days.

(21) Appl. No.: 11/710,734

(22) Filed: Feb. 26, 2007

(65) Prior Publication Data
US 2007/0161858 A1    Jul. 12, 2007

Related U.S. Application Data

(63) Continuation of application No. 10/790,327, filed on Mar. 1, 2004, now Pat. No. 7,195,588.

(51) Int. Cl.
*A61B 1/04* (2006.01)
*A61B 1/06* (2006.01)

(52) U.S. Cl. ........ 600/109; 600/160
(58) Field of Classification Search .......... 600/101, 600/103, 109, 118; 348/74
See application file for complete search history.

(56) References Cited

U.S. PATENT DOCUMENTS

| | | | |
|---|---|---|---|
| 5,209,220 A | 5/1993 | Hiyama et al. | |
| 5,387,928 A | 2/1995 | Nishimura | |
| 6,428,469 B1 | 8/2002 | Iddan et al. | |
| 6,683,643 B1 | 1/2004 | Takayama et al. | |
| 6,709,387 B1 | 3/2004 | Glukhovsky et al. | |
| 6,945,928 B2 | 9/2005 | Kobayashi et al. | |
| 2001/0051766 A1* | 12/2001 | Gazdzinski | 600/309 |
| 2002/0103417 A1 | 8/2002 | Gazdzinski | |
| 2002/0198439 A1 | 12/2002 | Mizuno | |
| 2004/0073819 A1* | 4/2004 | Sekine et al. | 713/300 |
| 2004/0087832 A1* | 5/2004 | Glukhovsky et al. | 600/118 |
| 2004/0092825 A1 | 5/2004 | Madar et al. | |
| 2004/0136596 A1* | 7/2004 | Oneda et al. | 382/232 |
| 2004/0165082 A1* | 8/2004 | Takai | 348/222.1 |

FOREIGN PATENT DOCUMENTS

| | | |
|---|---|---|
| EP | 1492352 A2 | 12/2004 |
| JP | 03-121037 | 5/1991 |
| JP | 03-123527 | 5/1991 |
| JP | 06-169395 | 6/1994 |
| JP | 06-266774 | 9/1994 |
| JP | 08-313823 | 11/1996 |

(Continued)

OTHER PUBLICATIONS

Japanese Office Action dated Oct. 6, 2009.

*Primary Examiner* — Philip R Smith
(74) *Attorney, Agent, or Firm* — Scully, Scott, Murphy & Presser, P.C.

(57) ABSTRACT

An image pick-up unit inserted in the body picks up an image of the body, and transmits by radio the image to an extra-corporeal unit which is arranged outside the body. The image pick-up unit includes an image pick-up portion capturing an image, a data transmitting portion for transmitting the image obtained by the image pick-up portion to the extra-corporeal unit at a plurality of transmitting ratios, a characteristic amount detecting portion for detecting a predetermined amount of characteristics based on the image, and a determining portion for determining a valid image based on an output from the characteristic amount detecting portion. The data transmitting portion controls the data transmitting ratio in accordance with the determining result of the determining portion.

10 Claims, 24 Drawing Sheets

FOREIGN PATENT DOCUMENTS

| | | |
|---|---|---|
| JP | 09-114985 | 5/1997 |
| JP | 10-229558 | 8/1998 |
| JP | 10-276974 | 10/1998 |
| JP | 10-294923 | 11/1998 |
| JP | 11-104072 | 4/1999 |
| JP | 2000-287094 | 10/2000 |
| JP | 2000-350085 | 12/2000 |
| JP | 2001-078016 | 3/2001 |
| JP | 2002-007458 | 1/2002 |
| JP | 2002-16920 | 1/2002 |
| JP | 2002-508201 | 3/2002 |
| JP | 2002-118756 | 4/2002 |
| JP | 2002-119463 | 4/2002 |
| JP | 2003-23637 | 1/2003 |
| JP | 2003-37768 | 2/2003 |
| JP | 2004-23656 | 1/2004 |
| JP | 2004-521662 | 7/2004 |
| WO | WO 99/30610 | 6/1999 |
| WO | WO 01/87377 A2 | 11/2001 |
| WO | WO 03/010967 A1 | 2/2003 |
| WO | WO 2009/027906 A1 | 3/2009 |

\* cited by examiner

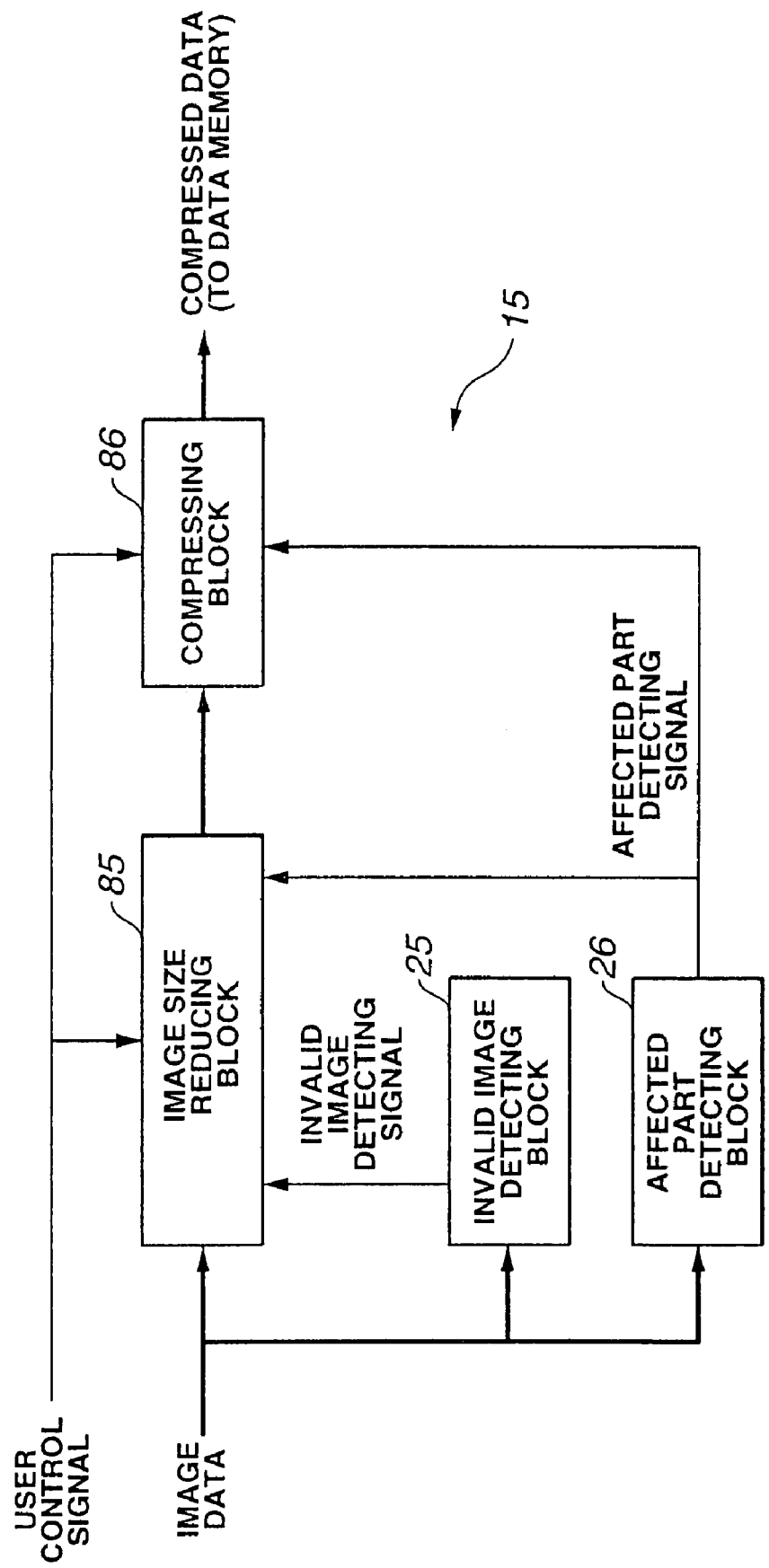

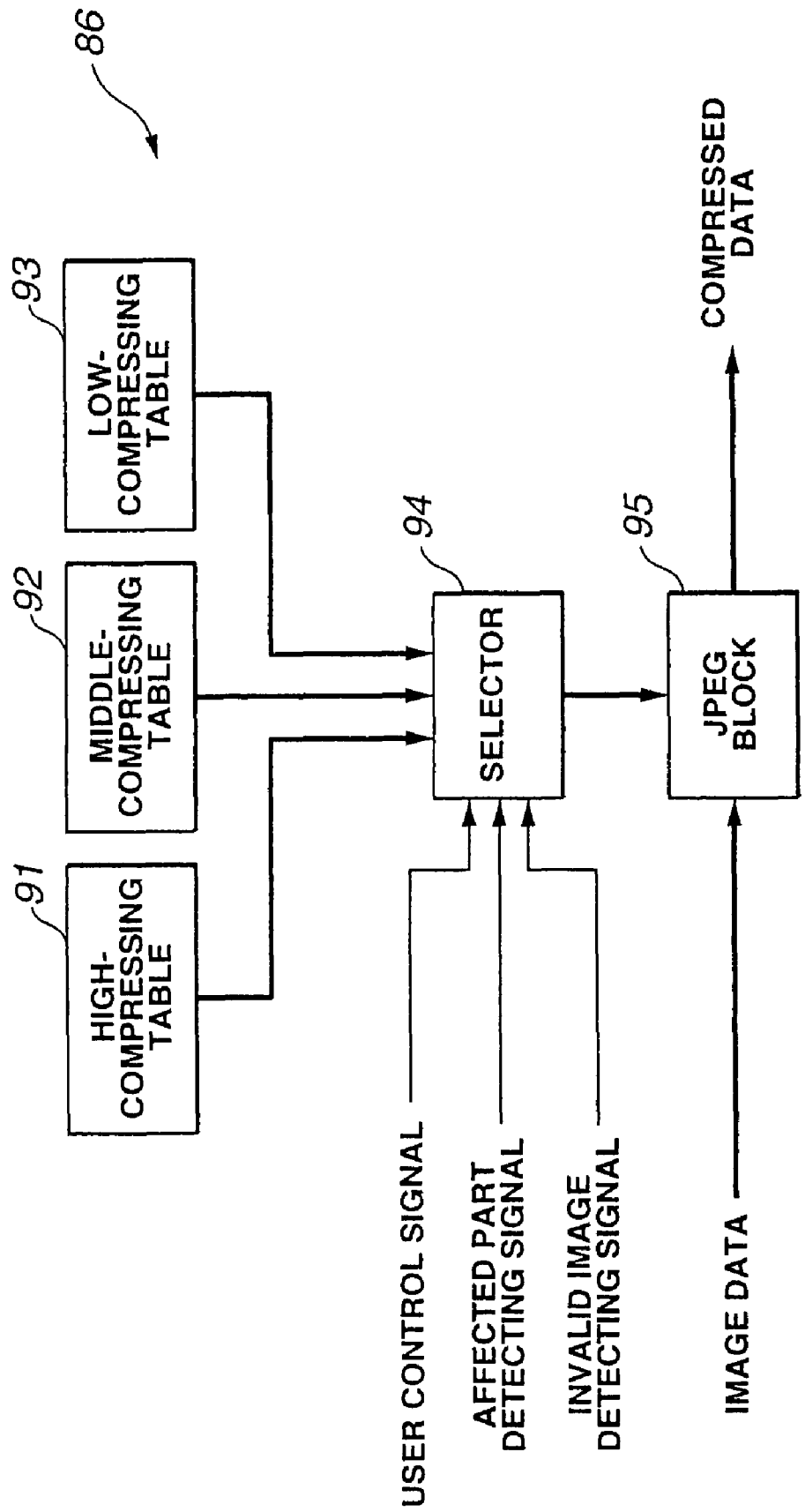

ENDOSCOPE IMAGE PICK-UP APPARATUS

This application is a continuation of U.S. patent Publication Ser. No. 10/790,327 filed on Mar. 1, 2004 now U.S. Pat. No. 7,195,588, and claims benefit of Japanese Application No. 2002-320239 filed on Nov. 1, 2002, the contents of which are incorporated by this reference.

BACKGROUND OF THE INVENTION

1. Field of the Invention

The present invention relates to an endoscope image pick-up apparatus in which an image in the body is picked up by an image pick-up unit and the resultant image is transmitted by radio to an extra-corporeal unit.

2. Description of the Related Art

For example, Japanese Unexamined Patent Application Publication No. 2002-508201 discloses, as a conventional art, an endoscope image pick-up apparatus in which an image in the body is picked up by an image pick-up unit and the resultant image is transmitted by radio to an extra-corporeal unit.

According to the conventional art, the image pick-up unit, which is inserted in the body, comprises an acceleration sensor as a movement detector in the axial direction. The acceleration sensor detects the movement in the axial direction, when the acceleration in the axial direction is lower than the preset threshold value, and a power source is shut off. Thus, the collection of redundant images is prevented and the consumption energy of the image pick-up unit is minimized.

SUMMARY OF THE INVENTION

According to the present invention, there is provided an endoscope image pick-up apparatus for picking up an image in the body by an image pick-up unit inserted in the body and for transmitting the image by radio to an extra-corporeal unit which is arranged outside the body, wherein the image pick-up unit comprises: an image pick-up device for capturing an image; a data transmitting device for transmitting the image obtained by the image pick-up device to the extra-corporeal unit at a plurality of transmitting ratios; a characteristic amount detecting device for detecting a predetermined amount of characteristics based on the image; and a determining device for determining a valid image based on an output from the characteristic amount detecting device, and the data transmitting device controls the data transmitting ratio in accordance with the determining result of the determining device.

BRIEF DESCRIPTION OF THE DRAWINGS

FIGS. 1 to 19B relate to the first embodiment of the present invention,
FIG. 1 is a schematic diagram showing a system according to the first embodiment;
FIG. 2 is a block diagram showing the schematic structure of an image pick-up unit;
FIG. 3 is a timing chart for the operation of the image pick-up unit;
FIG. 4 is a block diagram showing the structure of a processing block shown in FIG. 2;
FIG. 5 is a timing chart of the processing block;
FIG. 6 is a block diagram showing the structure of an invalid image detecting block shown in FIG. 4;
FIG. 7 is a block diagram showing the structure of a luminance range detecting block shown in FIG. 6;
FIG. 8 is a block diagram showing the structure of an image change detecting block shown in FIG. 6;
FIG. 9 is a block diagram showing the structure of an image change detecting block according to a modification;
FIG. 10 is a block diagram showing the structure of an affected part detecting block shown in FIG. 4;
FIG. 11 is a block diagram showing the structure of a specific color detecting block shown in FIG. 10;
FIG. 12 is a block diagram showing the structure of a specific-color change detecting block shown in FIG. 10;
FIG. 13 is a block diagram showing the structure of a color distribution characteristic detecting block shown in FIG. 10;
FIG. 15 is a block diagram showing the structure of a color space converting block;
FIG. 16 is a block diagram showing the structure of a hue histogram calculating block shown in FIG. 13;
FIG. 18 is a block diagram showing the structure of a hue distribution characteristic detecting block shown in FIG. 13;
FIGS. 19A and 19B are explanatory diagrams showing the operation of the hue distribution characteristic detecting block;
FIGS. 20 to 25 relate to the second embodiment of the present invention,
FIG. 20 is a block diagram showing the structure of a processing block according to the second embodiment;
FIG. 21 is a timing chart of the processing block;
FIG. 22A is a block diagram showing the structure of an image size reducing block;
FIG. 22B is a table showing states of the image size reducing block of FIG. 22A;
FIG. 23 is an explanatory diagram showing the operation of an image cutting-out block;
FIG. 24 is an explanatory diagram of the image reduction;
and
FIG. 25 is a block diagram showing the structure of a compressing block.

DESCRIPTION OF THE PREFERRED EMBODIMENTS

Hereinbelow, a description is given of embodiments of the present invention with reference to the drawings.

First Embodiment

The first embodiment of the present invention will be described with reference to FIGS. 1 to 19B. First, a description is given of the basic structure of a system according to the first embodiment with reference to FIGS. 1 to 3.

Figure 1:
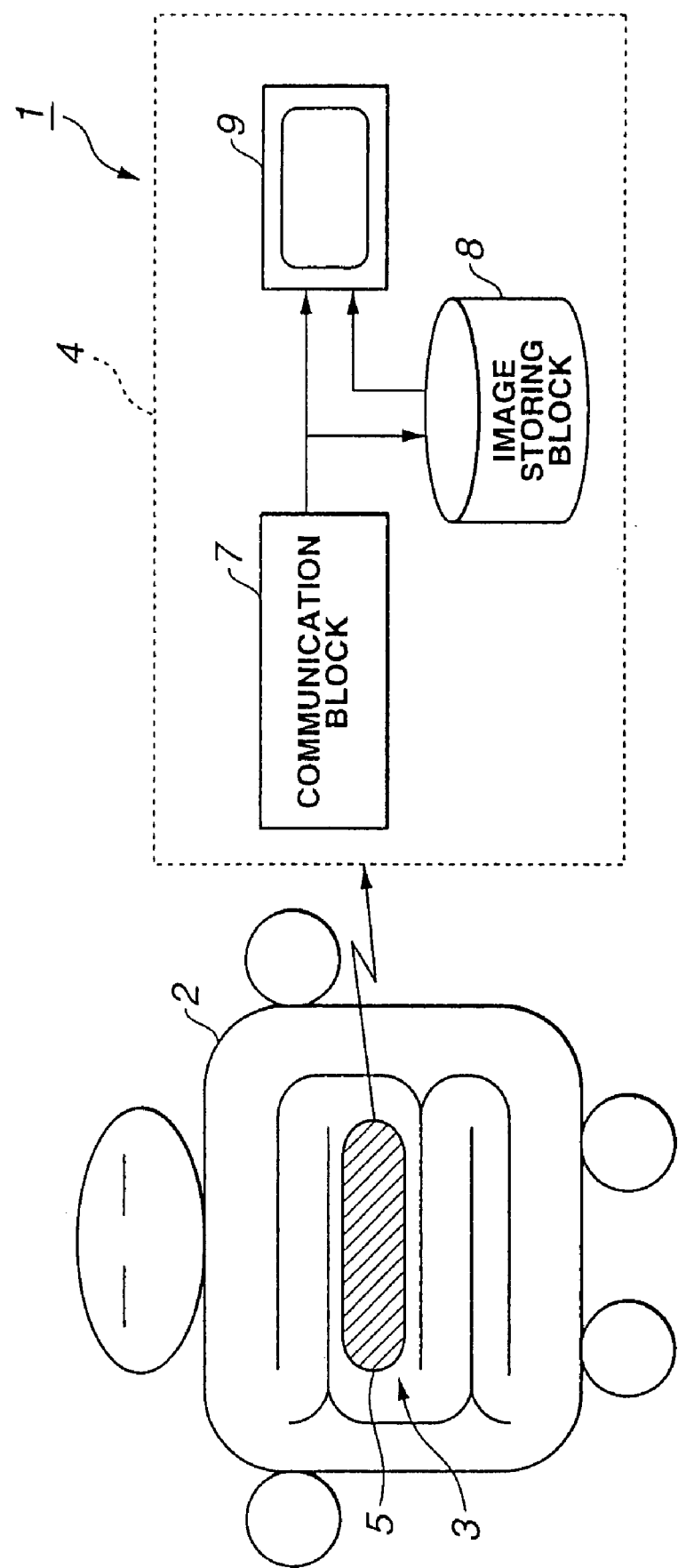

Referring to FIG. 1, an endoscope image pick-up apparatus or endoscope image pick-up system 1 comprises: an image pick-up unit 3 which is inserted in a body 2, then picks up an image of the body 2, and transmits image data thereof by radio; and an extra-corporeal unit 4 which receives the image data that is transmitted by radio from the image pick-up unit 3 and which stores and displays the image data.

Referring to FIG. 1 again, the image pick-up unit 3 comprises a capsule sealed container 5 which includes: blocks having an image pick-up block 13, which will be described later with reference to FIG. 2; and a battery 21. The image pick-up unit 3 supplies electric energy from the battery 21 to the image pick-up block 13 or the like, and transmits by radio, to the extra-corporeal unit 4 arranged outside the body, the image picked-up by the image pick-up block 13.

The extra-corporeal unit 4 receives and demodulates the image data which is modulated and transmitted by radio from the image pick-up unit 3 from a communication block 7. The extra-corporeal unit 4 stores the demodulated image data to an image storing block 8, transmits the image data to a monitor 9, and displays the picked-up image onto a display surface of the monitor 9. The extra-corporeal unit 4 transmits the image data stored in the image storing block 8 to the monitor 9 side and displays the image.

Figure 2:
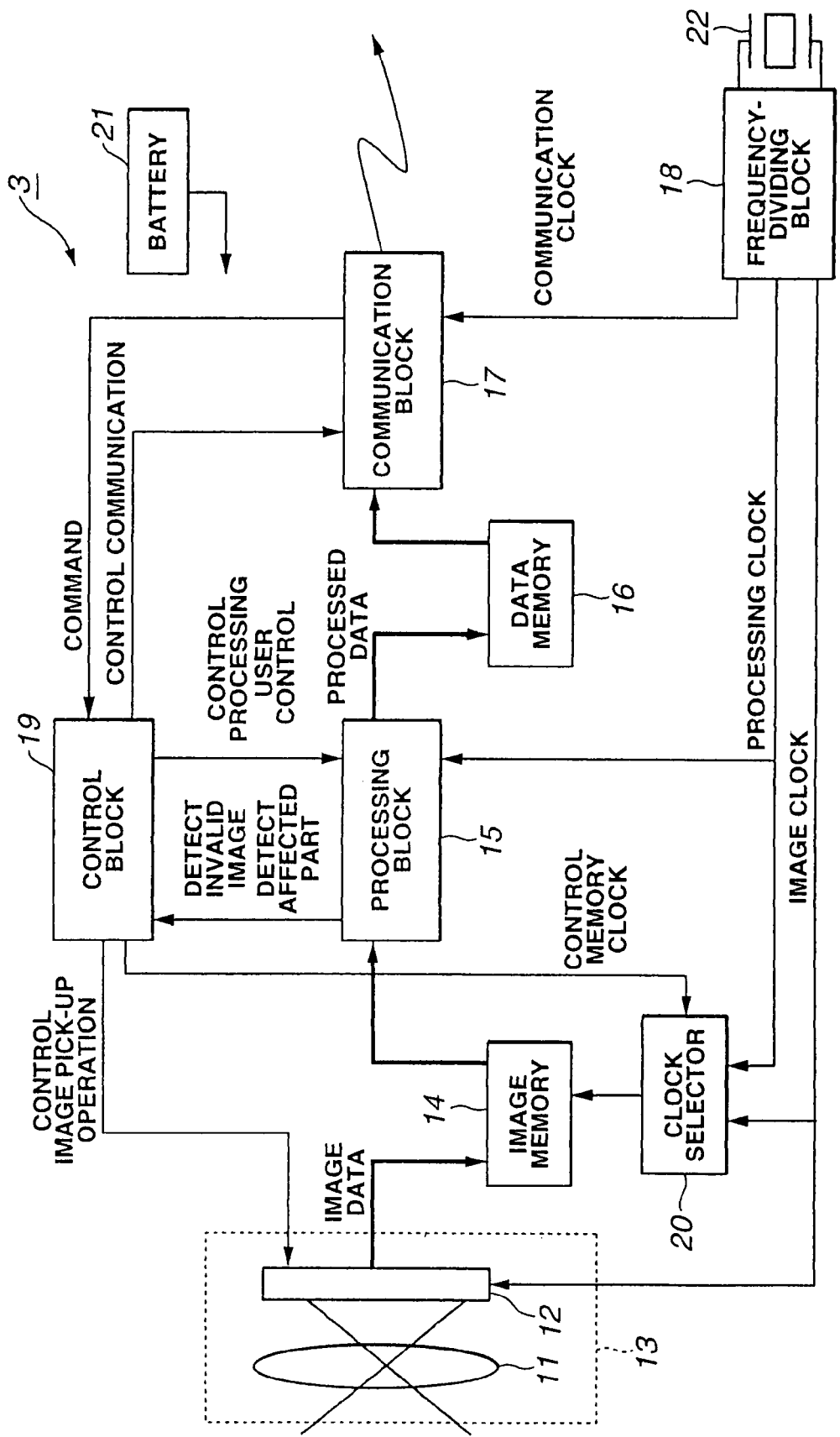

FIG. 2 shows the structure of an electric system in the image pick-up unit 3. The image pick-up unit 3 comprises: the image pick-up block 13 comprising an objective optical system 11 for forming an optical image of an examination target part in the body cavity into which the image pick-up unit 3 is inserted and a (solid-state) image pick-up device 12 such as a CCD or CMOS sensor; an image memory 14 which temporarily stores, via an A/D converter (not shown), digital image data picked-up by the image pick-up device 12; a processing block 15 which performs various processing of the image data stored in the image memory 14; and a data memory 16 which temporarily stores the data processed by the processing block 15.

The image pick-up unit 3 comprises: a communication block 17 which reads the processed data from the data memory 16, transmits the read data to the extra-corporeal unit 4, and receives a command for controlling the image pick-up unit 3 from the extra-corporeal unit 4; and a frequency-dividing block 18 which generates clocks necessary for the blocks.

The image pick-up unit 3 further comprises: a control block 19 which outputs a control signal to the blocks; a clock selector 20 which changes the processing speed of the image data; the battery 21 which supplies power for driving the blocks and electric devices such as the image pick-up device 12; and an illuminating block having a white LED (not shown) for illuminating the examination target part picked-up by the image pick-up block 13.

The control block 19 outputs an image pick-up control signal for controlling the image pick-up operation, a processing control signal for controlling the processing, a communication control signal for controlling the communication, and a memory clock control signal for switching the frequency of an image clock for reading and writing data in the image memory 14, to the image pick-up device 12, the processing block 15, the communication block 17, and the clock selector 20, respectively.

The processing block 15 detects a predetermined characteristic amount of the image from the image memory 14, which will be described later. Upon determining that the image is a valid portion, e.g., an affected part (or target image) based on the output of the characteristic amount, the processing block 15 outputs an affected part detecting signal to the control block 19. Upon determining that the image is invalid, the processing block 15 outputs an invalid image detecting signal to the control block 19. When a command is received from the extra-corporeal unit 4, the communication block 17 supplies the command to the control block 19.

According to the first embodiment, for the purpose of the minimization of the image pick-up unit 3, clocks generated by a single crystal oscillator 22 are frequency-divided by the frequency diving block 18, and a communication clock supplied to the communication block 17, a processing clock supplied to the processing block 15, an image clock supplied to the image pick-up device 12 and image memory 14 are generated, respectively.

As will be described according to the second embodiment, a user transmits the command from the extra-corporeal unit 4 to the control block 19 and thus the control block 19 transmits, to the processing block 15, a user control signal as a control signal transmitted by the user. Then, the processing operation of the processing block 15 is controlled.

Figure 3:
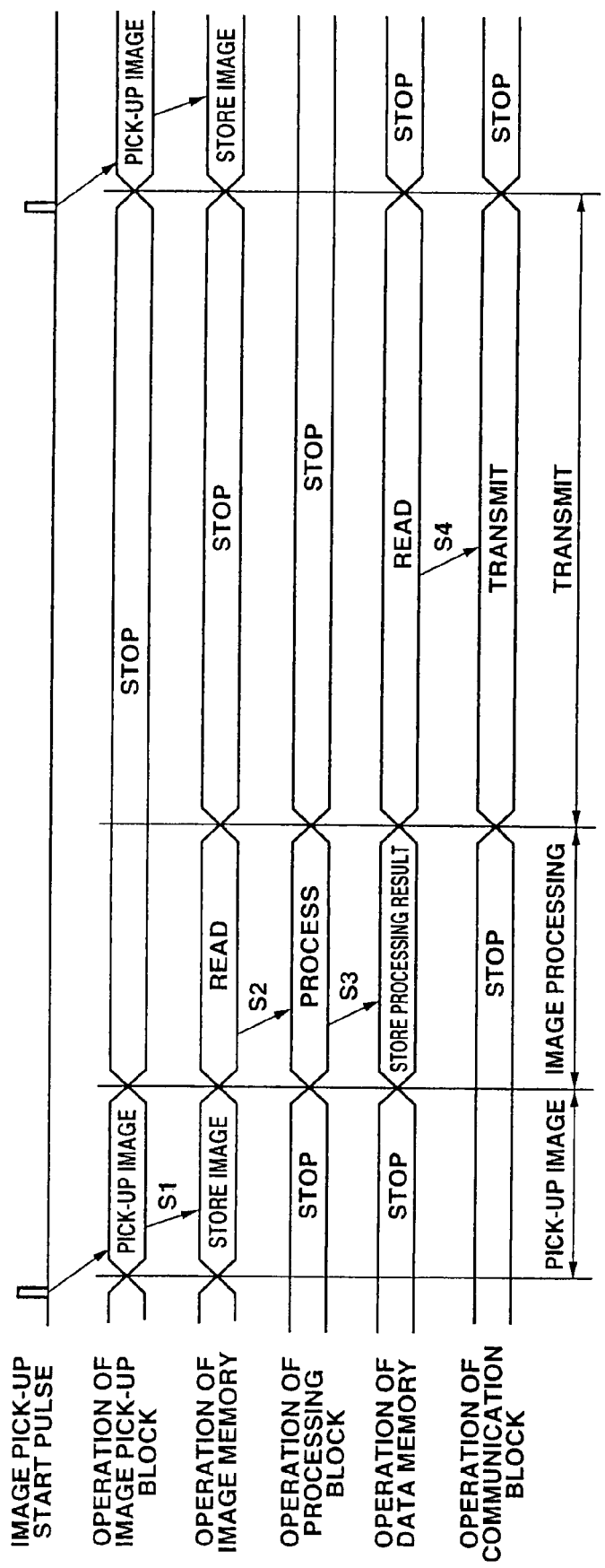

FIG. 3 shows a timing chart for the operation of the image pick-up unit 3.

An image pick-up start pulse is generated from a CPU (not shown) forming a controller of the control block 19 in order to transmit the image for a predetermined period. The image pick-up block 13 starts the image pick-up operation by the image pick-up start pulses and the picked-up image data is stored in the image memory 14 (this processing is shown by S1 in FIG. 3 and, similarly, the subsequent processing is shown by S2 and the like).

After storing the image data corresponding to one screen, the processing block 15 reads the image data from the image memory 14 (S2), performs the processing such as compression and characteristic detection, and stores the processing result thereof in the data memory 16 (S3). After ending the processing, the data stored in the data memory 16 is transmitted to the communication block 17, is modulated by the communication block 17, and is transmitted extra-corporeal unit 4 (S4).

In the basic system according to the first embodiment, referring to FIG. 3, the blocks have the sequence for preventing the simultaneous operation and thus the peak value of the consumption power from the battery 21 is reduced. That is, as shown by the bottom stage in FIG. 3, the sequence includes the sequential processing for time-dividing the image pick-up processing for picking up the image and storing the picked-up image, the imaging processing for reading the stored image, imaging the data, and storing the resultant data to the data memory 16, and the transmitting processing for reading the imaged data and transmitting the data.

As mentioned above, the image clock is supplied to the image memory 14 and the like.

The image signal needs a high-speed clock to some extent under the restriction of a frame rate.

Upon picking up the image, almost the blocks (internal block) are not operated, excluding the image pick-up block 13 in the image pick-up unit 3 shown in FIG. 3. Therefore, although the power consumption is not increased, almost the blocks in the image pick-up unit 3 are operated upon processing and transmitting the image signal. Thus, the power consumption is reduced by operating the internal blocks at a low-speed clock.

That is, the processing block 15 is operated at the processing clock speed lower than the image clock speed. Further, the communication block 17 is operated at the communication clock speed lower than the image clock speed.

In this case, the power consumption of the image memory 14 is reduced by using the clock selector 20 for switching the high-speed and low-speed clocks upon picking up and processing the image signal. That is, the control block 19 controls the clock selector 20 by a memory clock control signal, so that the image clock at the high speed is supplied upon the picking up the image and the processing clock at the low speed is supplied upon processing the data.

Figure 4:
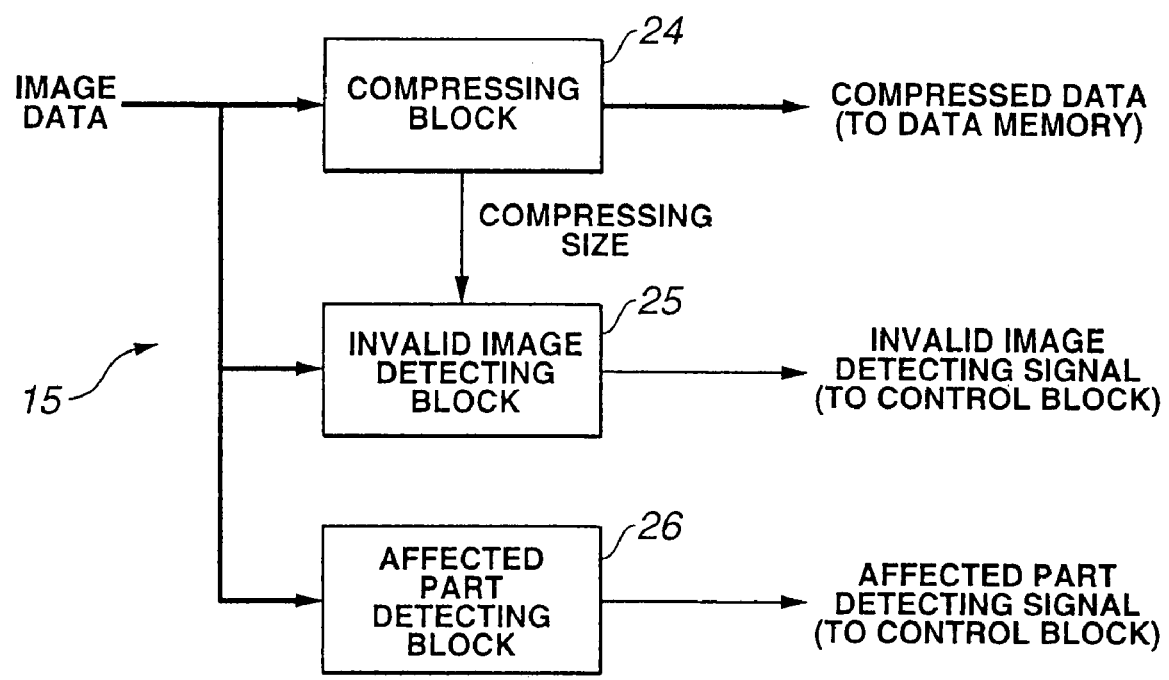

The detailed structure and operation will be described according to the first embodiment with reference to FIGS. 4 to 19B. FIG. 4 shows the structure of the processing block 15 according to the first embodiment.

The image data inputted to the processing block is inputted to a compressing block 24 for compressing the image data, and an invalid image detecting block 25 and an affected part detecting block 26 forming characteristic amount detecting means for detecting the characteristic amount based on the image data and determining means for determining the validity.

The compressing block 24 forms compressed data which is obtained by reducing the data amount by compressing the image data. Then, the compressing block 24 stores the compressed data to the data memory 16.

The invalid image detecting block 25 detects the characteristic amount for the invalidity such as the white compression and black compression in the image and no change in image, and further determines whether or not the image is invalid. If it is detected that the image is invalid, the invalid image detecting block 25 outputs an image invalid detecting signal.

The affected part detecting block 26 detects the characteristic amount for the affected part or the present or absence of the similar matter in the image data, and determines based on the detecting result whether or not the image is a target image. If it is detected that the image is the target image, the affected part detecting block 26 outputs an affected part detecting signal.

The invalid image detecting signal and affected part detecting signal are inputted to the control block 19. The control block 19 controls the next image pick-up timing and the transmission of the image data based on the invalid image detecting signal and the affected part detecting signal.

Figure 5:
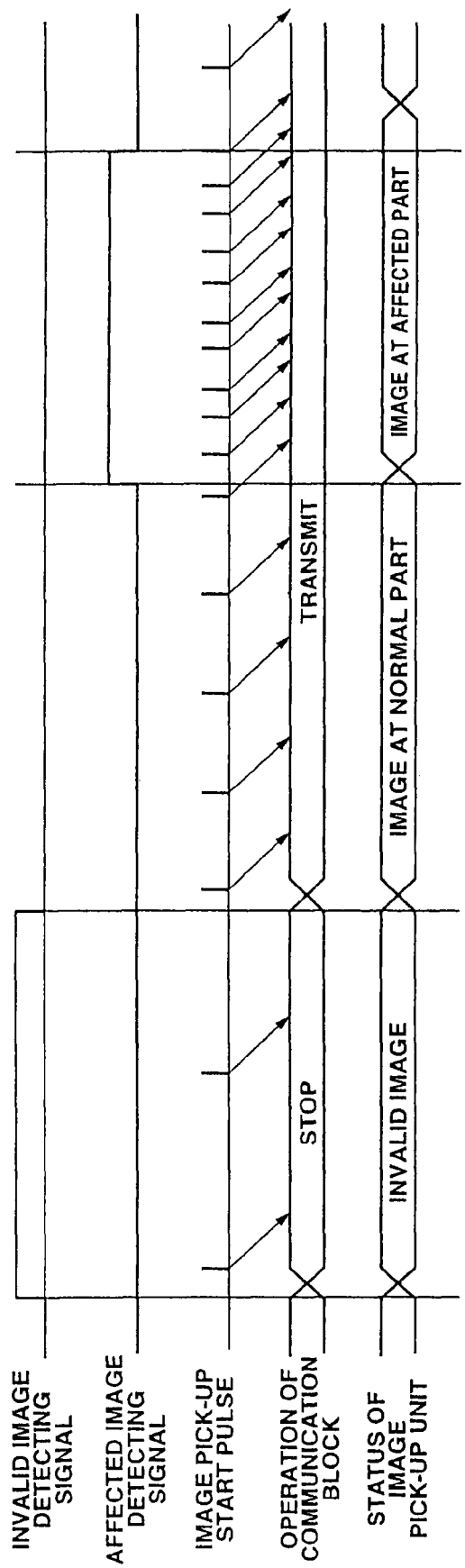

FIG. 5 shows a timing chart of the processing block 15.

First, when the invalid image detecting signal is active (H level), the processing block 15 does not transmit the image data and delays the next image pick-up period. Thus, the image which is determined as invalid and unnecessary is not subjected to the processing and the transmission (in this case, the status of the image pick-up unit 3 is referred to as an image invalid (status)).

When the invalid image detecting signal is not active and the affected part detecting signal is not active (H level), the image pick-up block 13 picks up the image for a predetermined period. The processing block 15 transmits the picked-up image as a normal-part image to the extra-corporeal unit 4 (in this case, the status of the image pick-up unit 3 is referred to as a normal-part image (status)).

Further, when the affected part detecting signal is active, it is considered that the target image is picked up. Therefore, the processing block 15 reduces the image pick-up and transmitting period so as to improve the diagnosis capacity, obtains a large amount of images around the affected part, and transmits the obtained image to the extra-corporeal unit 4 (in this case, the status of the image pick-up unit 3 is referred to as an affected-part image (status)).

According to the first embodiment, the processing block 15 detects the characteristic amount of the picked-up image, determines whether or not the image is valid, that is, whether the characteristic amount includes an invalid portion or valid portion, and controls a transmitting ratio of the image data transmitted to the extra-corporeal unit 4 from the communication block 17 in accordance with the determining result.

If it is determined that the image includes the invalid portion, the processing block 15 controls the transmitting ratio to be stopped. If it is determined that the image is the normal image, the processing block 15 controls the transmitting ratio to the normal transmitting ratio. Further, if it is determined that the image includes the valid portion such as the affected part, the processing block 15 controls the transmitting ratio to be increased.

As controlled above, the power of the battery 21 is consumed to transmit the image data with the large amount of information. The power consumption of the battery 21 is automatically adjusted in the proper state by increasing the transmitting ratio of the valid image necessary for the user and then by reducing the transmitting ratio of another image.

In addition to the above-mentioned operation, the control block 19 controls the image pick-up and transmitting periods by receiving the command from the extra-corporeal unit 4. Further, the control block 19 invalidates the control of the image pick-up and transmitting period in the image pick-up unit 3 by receiving another command. The control operation based on the command from the extra-corporeal unit 4 is prior and the image pick-up and transmitting period is controlled.

Thus, when the difficult determination is performed on the extra-corporeal unit 4, the determining result is transmitted to the image pick-up unit 3 by the command, and the image pick-up and transmitting ratio of the image pick-up unit 3 is controlled by the command.

Next, a description is given of the detailed structure of the blocks and the operation thereof.

Figure 6:
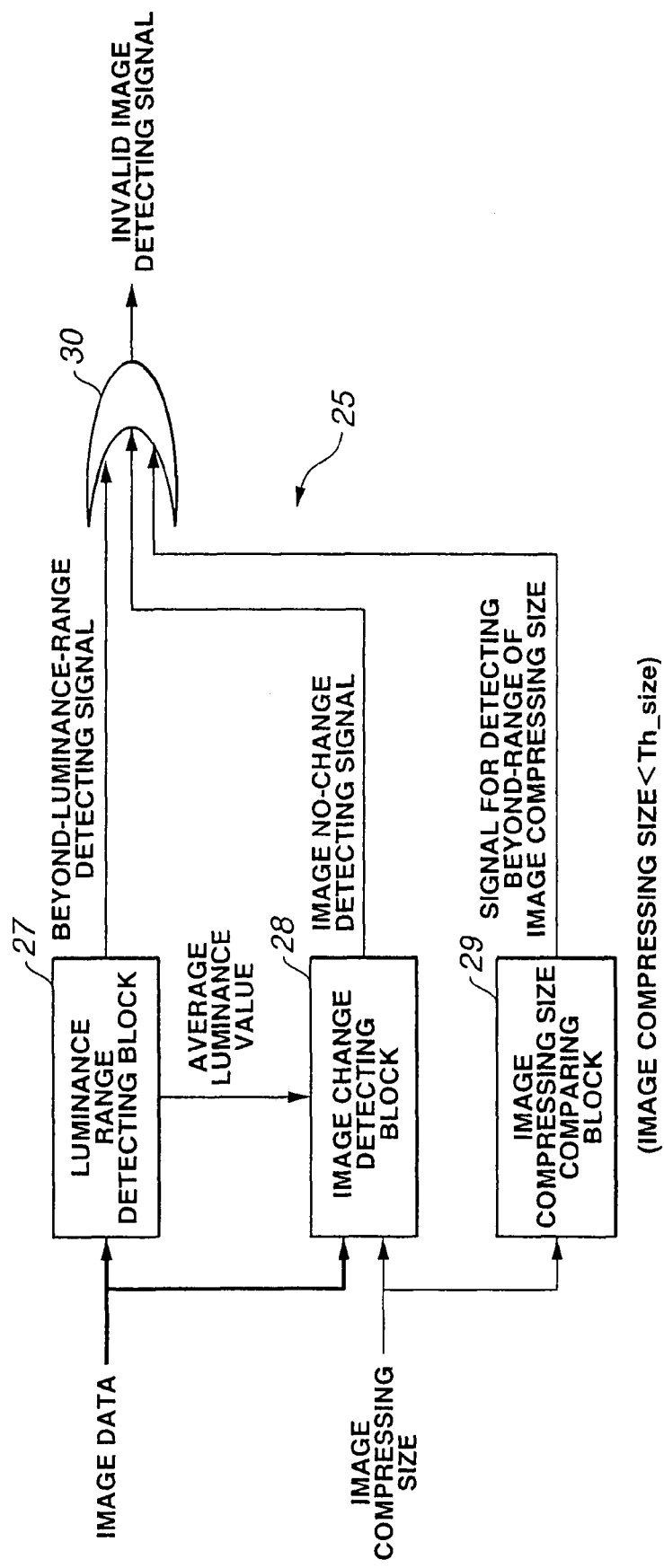

FIG. 6 shows the structure of the invalid image detecting block 25 shown in FIG. 4.

The invalid image detecting block 25 comprises: a luminance range detecting block 27; an image change detecting block 28; an image compressing size comparing block 29; and an OR circuit 30 to which the outputs signals therefrom are inputted.

The luminance range detecting block 27 detects the average value of the luminance value, and outputs, to the OR circuit 30, an beyond-luminance-range detecting signal when it is extremely bright or extremely dark. The image change detecting block 28 detects that the image does not change, that is, whether the image pick-up unit 3 does not move or moves in the body based on the image data, average luminance value, and (image) compressing size, and outputs an image non-change detecting signal to the OR circuit 30.

The image compressing size comparing block 29 compares the compressing size of image with a threshold value (Th_size). If it is determined that the compressing size of image is the threshold value (Th_size) or less, e.g., when the image is not focused with blur, the image compressing size comparing block 29 outputs, to the OR circuit 30, a signal for detecting the beyond-compressing-size of image. If it is determined that the compressing size of image is more than the threshold value (Th_size), the image compressing size comparing block 29 outputs the invalid image detecting signal to the control block 19 via the OR circuit 30.

Referring to FIG. 6, symbols ( ) denotes the operation for comparing the compressing size of image with the threshold value (Th_size) by the image compressing size comparing block 29 on the bottom. The foregoing comparing operation is similarly applied to another drawings.

Figure 7:
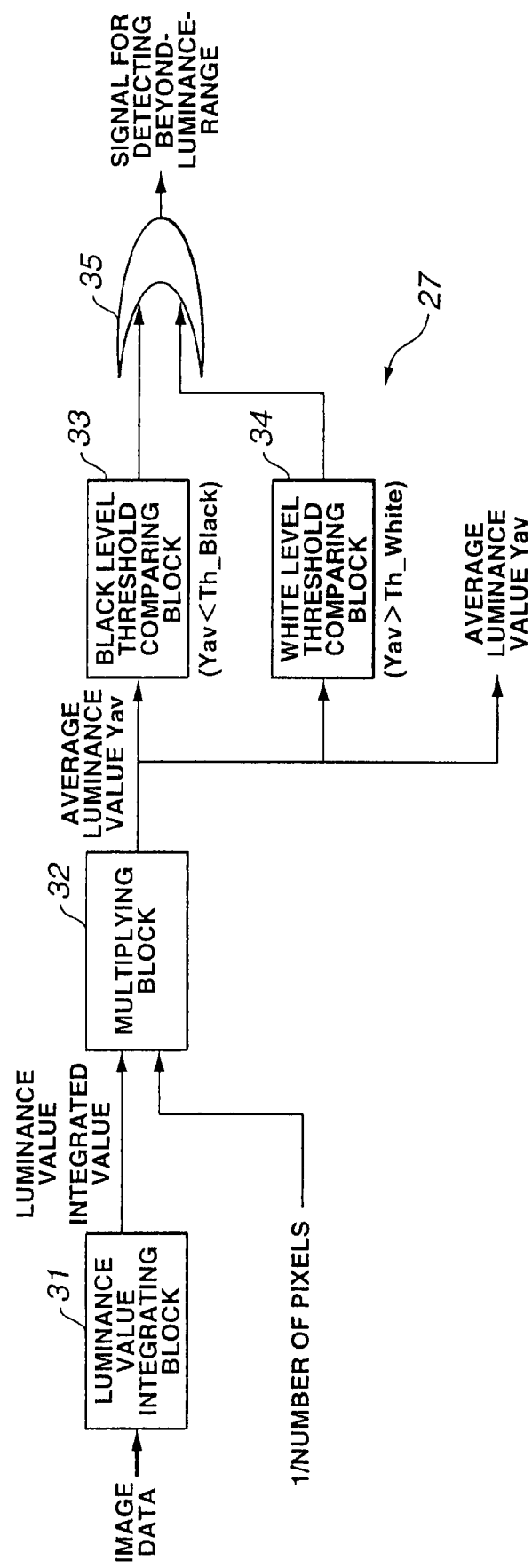

FIG. 7 shows the structure of the luminance range detecting block 27 shown in FIG. 6.

The luminance range detecting block 27 comprises: a luminance value integrating block 31 for integrating the luminance values of all the pixels of the inputted pixel signals; and a multiplying block 32 for calculating an average luminance value Yav of the image signal by dividing the integrated value of luminance values from the luminance value integrating block 31 by the number of pixels or multiplying it by 1/(number of pixels).

The luminance range detecting block 27 further comprises: a black level threshold value comparing block 33 for comparing whether or not the average luminance value Yav outputted from the multiplying block 32 is lower than a threshold value (Th_Black) of the black level; a white level threshold value comparing block 34 for comparing whether or not it is higher than a threshold value (Th_White) of the white level; and an OR circuit 35 into which output signals from the black level threshold value comparing block 33 and white level threshold value comparing block 34 are inputted.

The luminance range detecting block 27 outputs, from the OR circuit 35, a beyond-luminance-range signal indicating the determining result whether or not the image is extremely dark or extremely bright.

Figure 8:
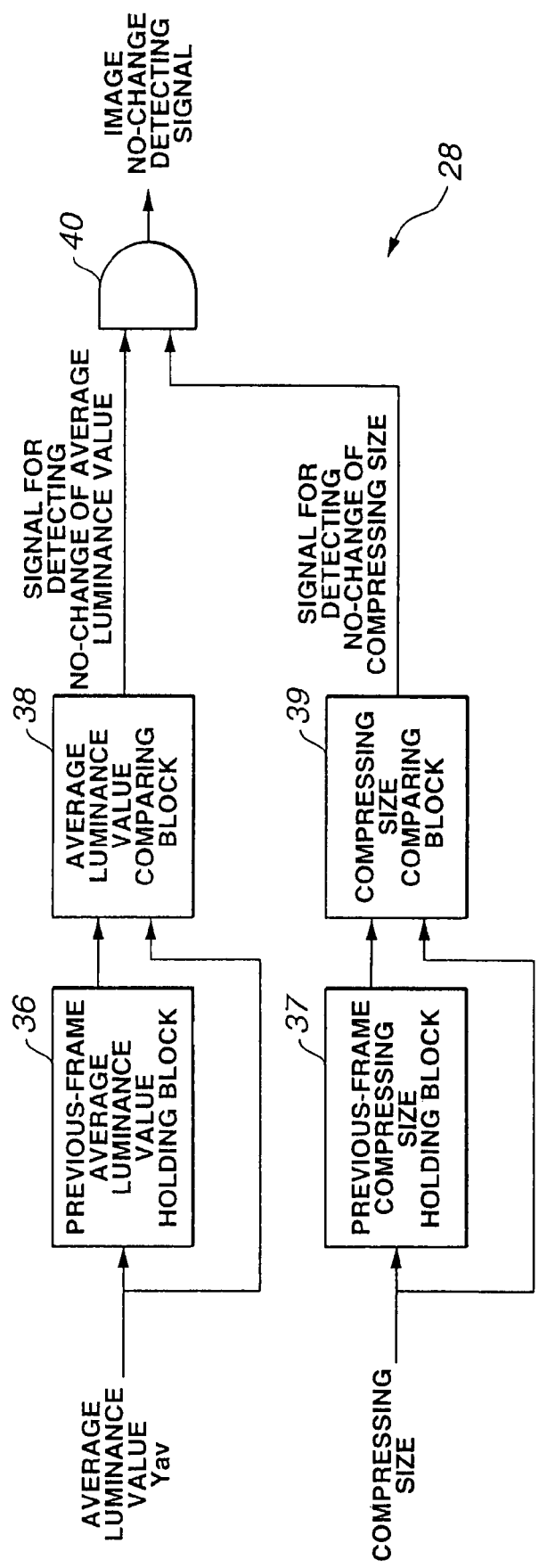

FIG. 8 shows an example of the image change detecting block 28 shown in FIG. 6. The image change detecting block 28 detects the image change based on the average luminance value Yav and the compressing size outputted from the compressing block 24.

Therefore, the average luminance value Yav and the compressing size are held in a previous-frame average luminance value holding block 36 and a previous-frame compressing size holding block 37 holding the average luminance value Yav and the compressing size of the frame before one frame.

The average luminance value Yav before one frame and the average luminance value Yav of the current frame are inputted to an average luminance value comparing block 38. The compressing size before one frame and the compressing size of the current frame are inputted to a compressing size comparing block 39.

The average luminance value comparing block 38 and compressing size comparing block 39 calculate the difference in average luminance values between the previous frame and the current frame and the difference in compressing sizes therebetween, respectively. If the absolutes of the difference are within a predetermined range, it is determined that the image does not change and the non-change detecting signal of the average luminance value and compressing size is outputted to an AND circuit 40.

The AND circuit 40 outputs the image non-change detecting signal by the AND operation of the two non-change detecting signals of the average luminance value and compressing size.

Figure 9:
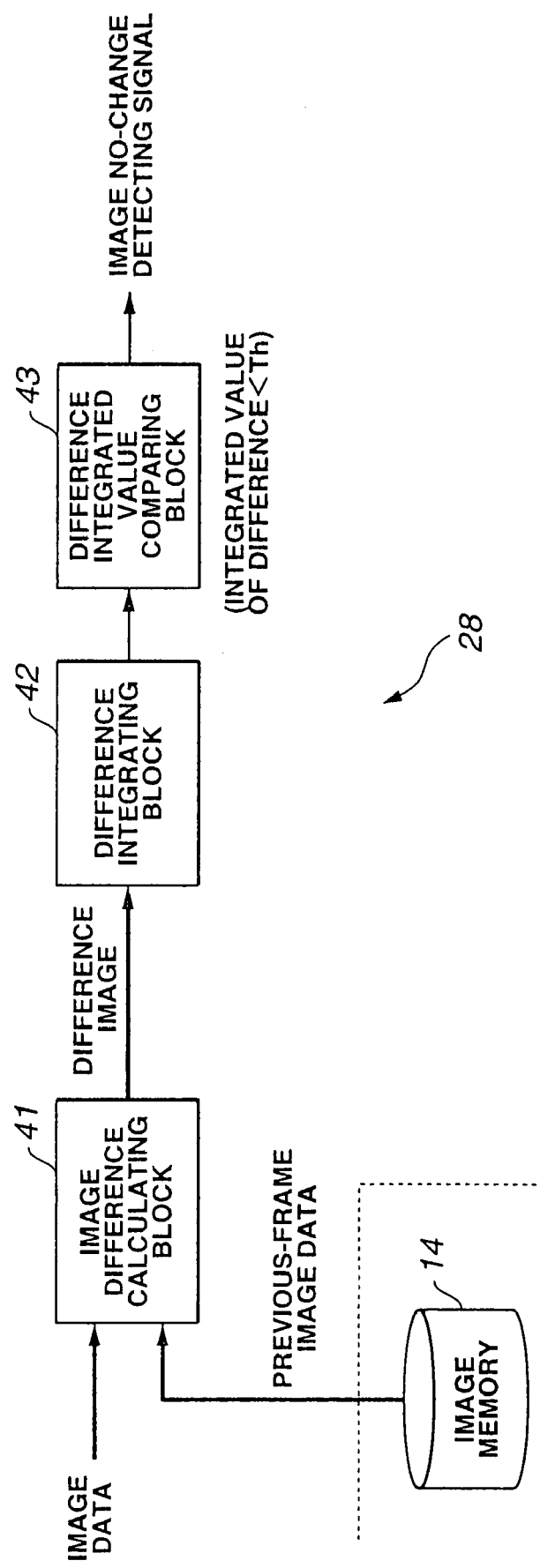

FIG. 9 shows the image change detecting block 28 according to a modification. According to the modification, the image change detecting block 28 reads the image of the current frame and the image of the previous frame from the image memory 14 shown in FIG. 2, and inputs both the images to an image difference calculating block 41.

The image difference calculating block 41 calculates the difference between the current frame and the previous frame every pixel, and inputs the resultant difference image to a difference integrating block 42, thus to calculate the integrated value. The integrated value is inputted to a difference integrated value comparing block 43.

The difference integrated value comparing block 43 compares the integrated value of one frame with a predetermined threshold value (e.g., Th). If it is determined that the integrated value is lower than the threshold value, the difference integrated value comparing block 43 determines that the image does not change and outputs the image non-change detecting signal.

If it is determined that the image is not worth viewing, that is, the image is extremely bright or extremely dark, or the image is the same as that transmitted before, the difference integrated value comparing block 43 does not transmit the image data. Thus, the power consumption of the battery 21 is reduced.

Figure 10:
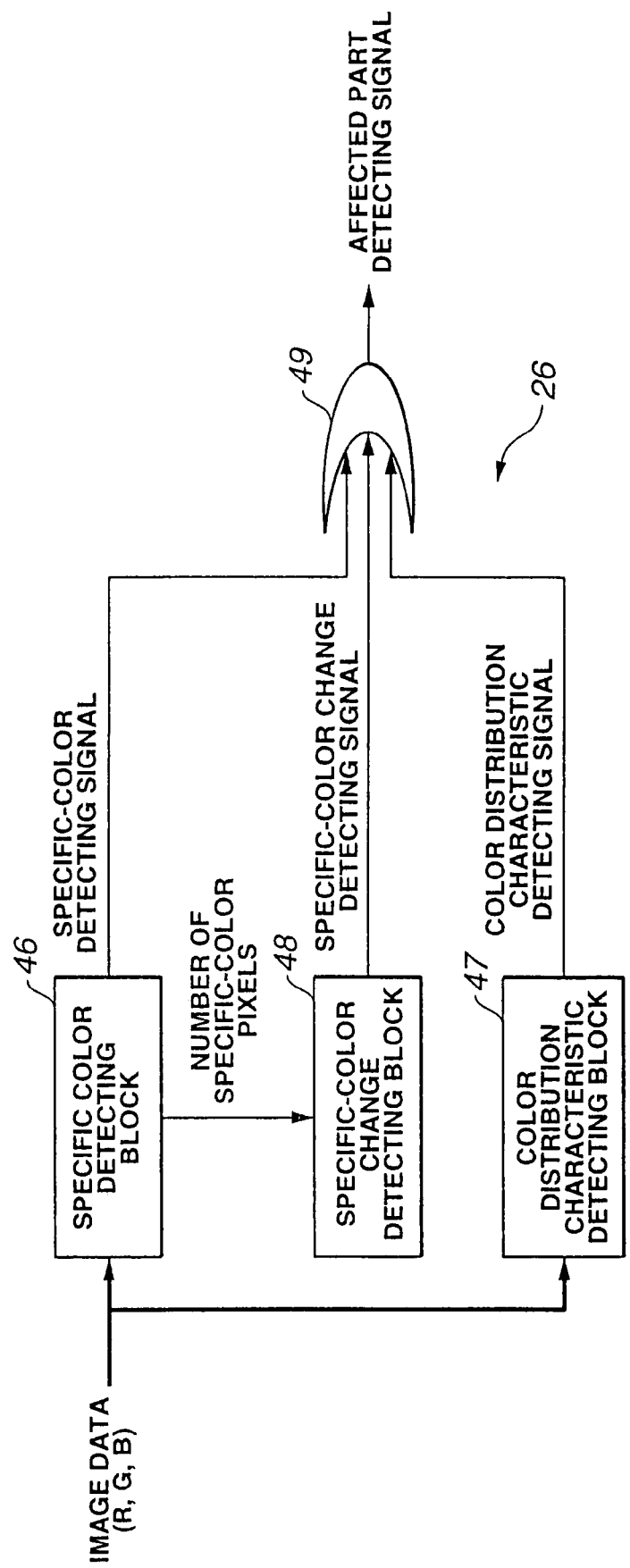

FIG. 10 shows the structure of the affected part detecting block 26 shown in FIG. 4.

According to the first embodiment, the affected part detecting block 26 detects the affected part which color-changes from the normal part (ulcer, tumor, hemorrhage, etc.), and comprises: a specific color detecting block 46 and a color distribution characteristic detecting block 47 for receiving image data (R, G, and B); a specific-color change detecting block 48 for detecting the change in specific color based on the number of pixels of the specific color from the specific color detecting block 46; and an OR circuit 49 for receiving the output signals from the three blocks 46 to 48.

The specific color detecting block 46 for receiving the image data (R, G, and B) detects the affected part by determining whether or not the affected part has a predetermined number of pixels in the stated or specific color space. In this case, the specific color detecting block 46 outputs a specific-color detecting signal to the OR circuit 49.

Further, the specific-color change detecting block 48 detects the affected part in the case that number of pixels in the stated color space, namely number of pixels in the specific color has changed. In this case, the specific-color change detecting block 48 outputs a specific-color change detecting signal to the OR circuit 49.

The color distribution characteristic detecting block 47 detects the affected part based on the characteristics including the hue and saturation of the inputted image data, and outputs a color distribution characteristic detecting signal to the OR circuit 49 in this case. The change of specific color and the color distribution are detected in parallel therewith and thus the color-changed affected part having some individual difference can accurately be detected.

In the case shown in FIG. 10, upon detecting any of the specific color detecting signal, specific-color change detecting signal, and color distribution characteristic detecting signal, the affected part detecting signal is outputted to the control block 19 via the OR circuit 49.

Figure 11:
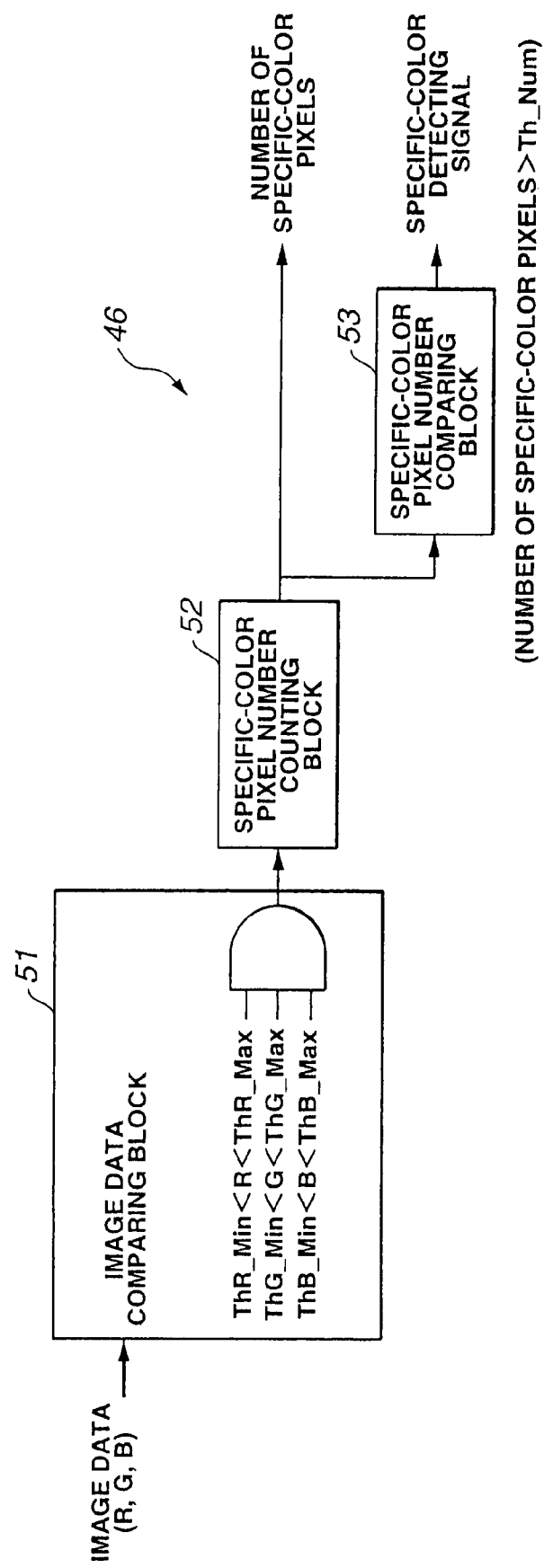

The structures and operations of the blocks shown in FIG. 10 will be described hereinbelow. FIG. 11 shows the structure of the specific color detecting block 46.

The specific color detecting block 46 compares the values (R, G, and B shown in FIG. 10 according to the first embodiment) of the image signals with the threshold value, that is, detects whether or not they are within a predetermined range by an image data comparing block 51.

Referring to FIG. 11, the image data comparing block 51 the values of the image signals (R, G, and B) with Th_Min<R<Th_Max, Th_Min<G <Th_Max, and Th_Min<B<Th_Max. Further, image data comparing block 51 outputs the resultant data to the AND circuit and obtains the result of the logical product from the AND circuit.

When all the image signals (R, G, and B) are within the predetermined range, the image data comparing block 51 outputs the resultant data as the specific-color pixel to a specific-color pixel number counting block 52 at the next stage. Further, the specific-color pixel number counting block 52 counts the number of pixels.

Thus, the specific-color pixel number counting block 52 detects the value (number of specific pixels) shared by the specific-color pixel in the image. The number of specific-color pixels is inputted to the specific-color change detecting block 48 shown in FIG. 10 and are inputted to a specific-color pixel number comparing block 53 shown in FIG. 11.

The specific-color pixel number comparing block 53 compares the number of specific-color pixels with a predetermined threshold value Th_Num, and determines the detection of the specific color of the affected part if it is determined that the number of specific-color colors is Th_Num or more. The (value of) the number of specific-color pixels is outputted to the specific color detecting block 46.

Figure 12:
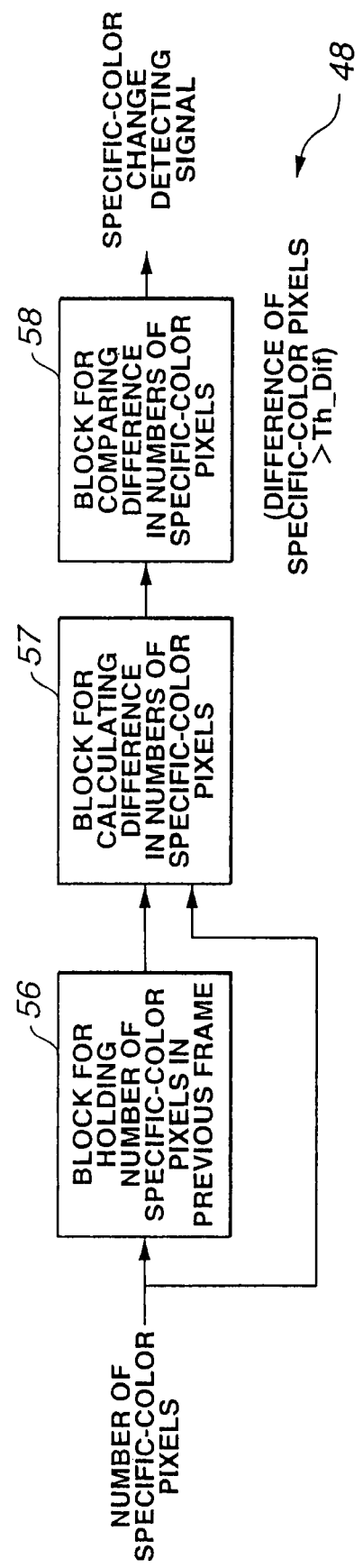

FIG. 12 shows the structure of the specific-color change detecting block 48 shown in FIG. 10.

A block 56 for holding the number of specific-color pixels in the previous frame and a block 57 for calculating the difference in number of specific-color pixels form the specific-color change detecting block 48. The number of specific-color pixels are inputted to the block 56 for holding the number of specific-color pixels in the previous frame and block 57 for calculating the difference in number of specific-color pixels from the specific color detecting block 46. The block 56 for holding the number of specific-color pixels in the previous frame holds the number of specific-color pixels of the previous frame.

The block 57 for calculating the difference in number of specific-color pixels calculates the difference in number of specific-color pixels between the previous frame and the current frame, and inputs the calculating result to a block 58 for comparing the difference in number of specific-color pixels. The block 58 for comparing the difference in number of specific-color pixels compares the difference with a threshold value Th_Dif, that is, determines whether or not the difference is a predetermined value or more. If it is determined that the difference is the threshold value Th_Dif or more, the change in specific color is detected and a specific-color change detecting signal is outputted.

Figure 13:
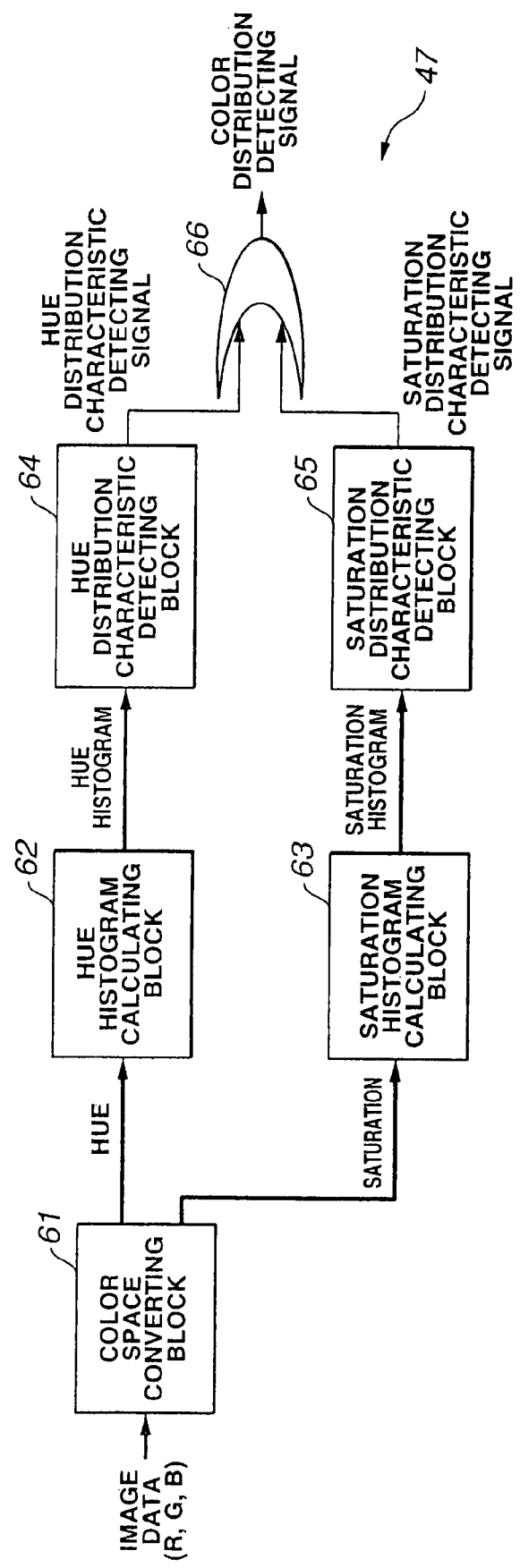

FIG. 13 shows the structure of the color distribution characteristic detecting block 47 shown in FIG. 10.

A color distribution characteristic detecting block 47 converts the inputted R-, G-, and B-images into the hue and saturation by a color space converting block 61. Next, a hue histogram calculating block 62 and a saturation histogram calculating block 63 detect the histograms (frequency distributions) of hue and saturation.

(Data of) the hue histogram and saturation histogram are inputted to a hue distribution characteristic detecting block 64 and a saturation distribution characteristic detecting block 65. The hue distribution characteristic detecting block 64 and saturation distribution characteristic detecting block 65 detect whether or not the histograms have predetermined characteristics, which will be described later. If it is determined that the histograms have the predetermined characteristics, the hue distribution characteristic detecting block 64 and saturation distribution characteristic detecting block 65 output, to an OR circuit 66, a signal for detecting the characteristic of the hue distribution and a signal for detecting the characteristic of the saturation distribution.

If it is detected that the histogram of any of the hue and saturation has the predetermined characteristic, a signal for detecting the characteristic of the color distribution is outputted via the OR circuit 66.

FIGS. 14A to 14F show examples of the characteristics of the color distribution of the hue and saturation of the affected part.

Figure 14A:
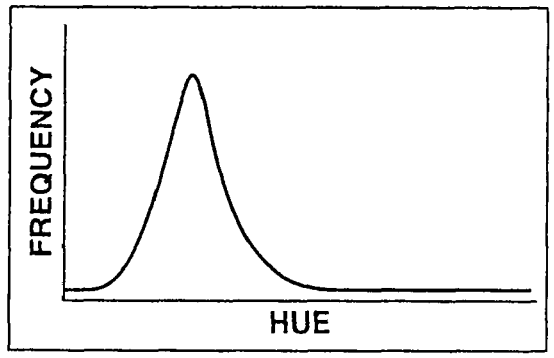
FIGS. 14A to 14F are diagrams showing examples of the hue and saturation at a normal part and a color-changed part.
Figure 14B:
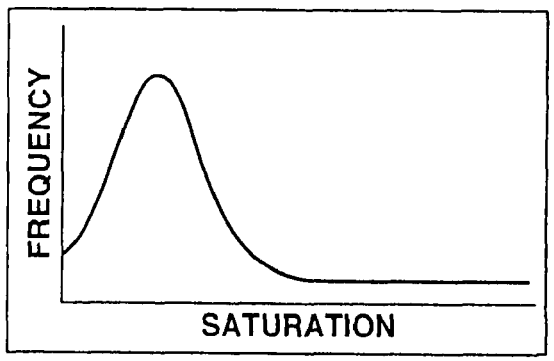

FIGS. 14A and 14B show the example of characteristics of the hue and saturation at the normal part. Since the internal organ photographed at the normal part is uniform, the hue and saturation have the peak at one place.

Figure 14C:
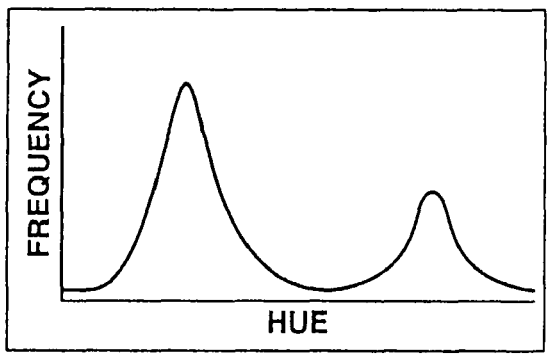
Figure 14D:
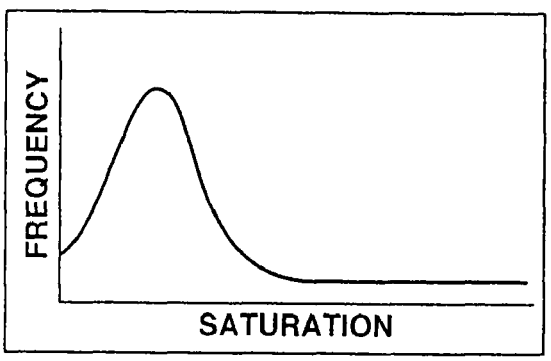

FIGS. 14C and 14D show examples of the characteristics of the hue and saturation in the case of photographing the color-changed part in which the changed color is generated by the ulcer or tumor. Since the hue at a part of the image is different, another peak is generated in addition to the peak of the normal part.

Figure 14E:
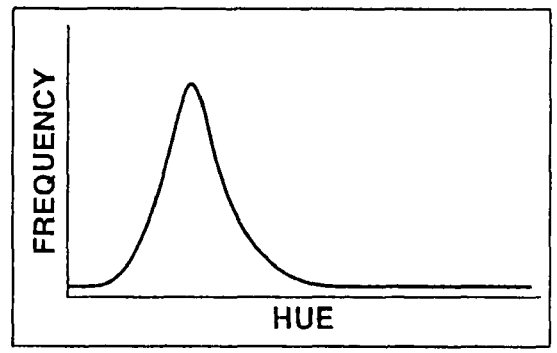
Figure 14F:
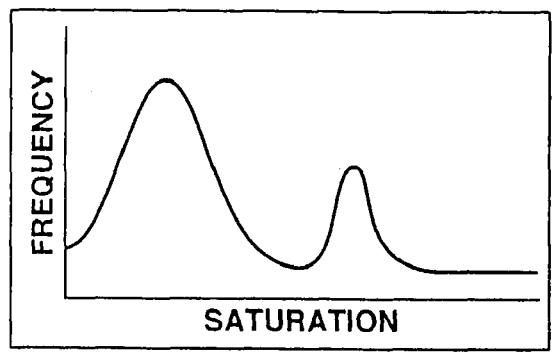

FIGS. 14E and 14F show example of the characteristics of the hue and saturation in the case of photographing a part in which the color change is caused by the hemorrhage or the like. Although the hue is not changed in this case, the hue at the normal part is different from that of the hemorrhage.

Therefore, the hue has another peak which is generated at the normal part in addition to the peak at the normal part.

As mentioned above, when the image has the color-changed portion, the histograms of hue and saturation have a plurality of peaks at a predetermined distance.

Next, the detailed operation of blocks will be described.

Figure 15:
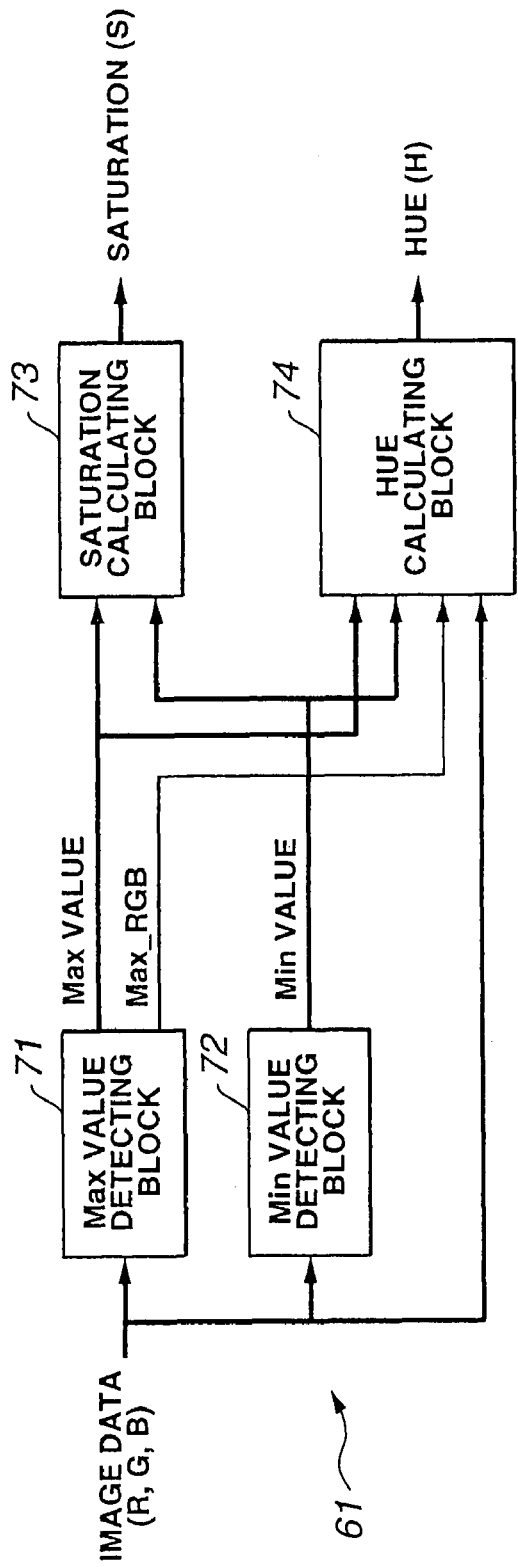

FIG. 15 shows one example of the color space converting block 61 shown in FIG. 13. The color space converting block 61 converts the image data inputted in the RGB space into the hue (H) and saturation (S).

Thus, the image data is inputted to a Max value detecting block 71 and a Min value detecting block 72. The Max value detecting block 71 and the Min value detecting block 72 compare the R-, G-, and B-values of the pixels in the inputted image data, select the maximum value and the minimum value, and output the selected values as a Max value and a Min value to a saturation calculating block 73 and a hue calculating block 74. The Max value detecting block 71 outputs, to the hue calculating block 74, a Max_RGB signal indicating that the Max value is any of R, G, and B. The image data is inputted to the hue calculating block 74.

The saturation calculating block 73 calculates the following saturation S.

$$\text{Saturation } S=(\text{Max value}-\text{Min value})/(\text{Max value})$$

The saturation is calculated based on the above-mentioned Max value and Min value.

The hue calculating block 74 calculates the hue value by the following calculation based on a Max_RGB signal indicating the Max value is any of R, G, and B.

That is, when R has the Max value, $$\text{Hue } H=(G-B)/(\text{Max}-\text{Min}).$$

Further, when G has the Max value, $$\text{Hue } H=2+(B-R)/(\text{Max}-\text{Min}).$$

Furthermore, when B has the Max value, $$\text{Hue } H=4+(R-G)/(\text{Max}-\text{Min})$$

As mentioned above, the hues are calculated.

Figure 16:
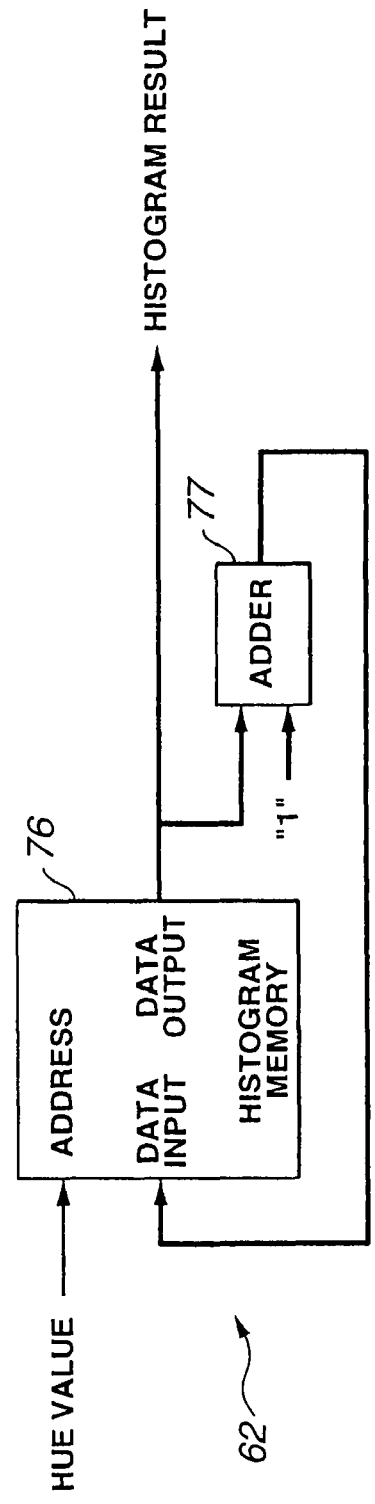

FIG. 16 shows the structure of the hue histogram calculating block 62 shown in FIG. 13. The hue histogram calculating block 62 comprises a histogram memory 76 and an adder 77 for adding one.

Figure 17A:
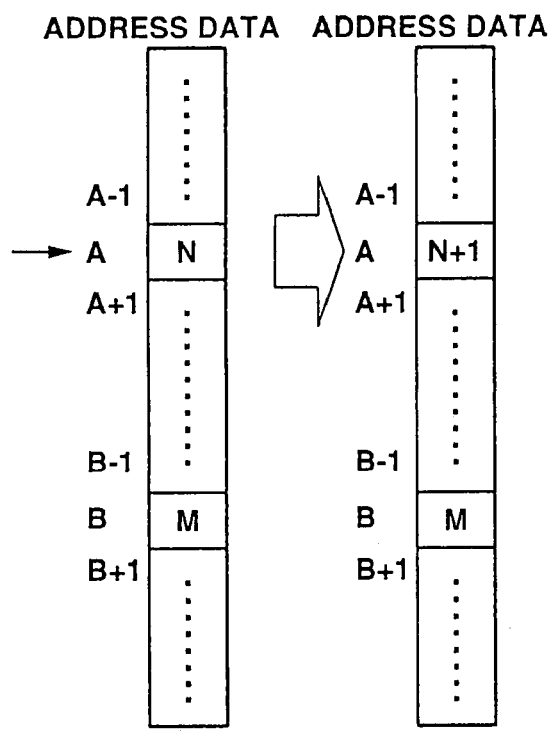
FIG. 17A is an operation diagram of a histogram memory upon inputting a hue value to an address A shown in FIG. 16.
Figure 17B:
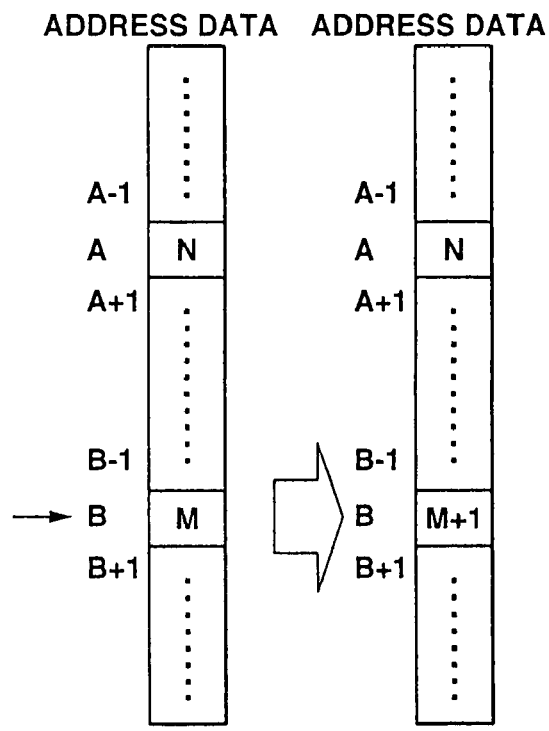
FIG. 17B is an operation diagram of the histogram memory upon inputting a hue value to an address B shown in FIG. 16.

The hue value is inputted to the address of the histogram memory 76. After inputting the hue value, the value stored in the address is incremented by 1. FIGS. 17A and 17B show the operation of the histogram memory 76.

FIG. 17A shows the case of inputting a hue value. Data N stored in the address A is incremented by 1 and data (N+1) is stored. FIG. 17B shows the case of inputting a hue value. Data M stored in the address B is incremented by 1, and data (M+1) is added. By repeating the above operation for all the pixels, the frequency distribution of the hue values is stored in the histogram memory 76.

The saturation histogram calculating block 63 shown in FIG. 13 has the above-mentioned structure. Thus, the structure and operation of the saturation histogram calculating block 63 are not described here.

Figure 18:
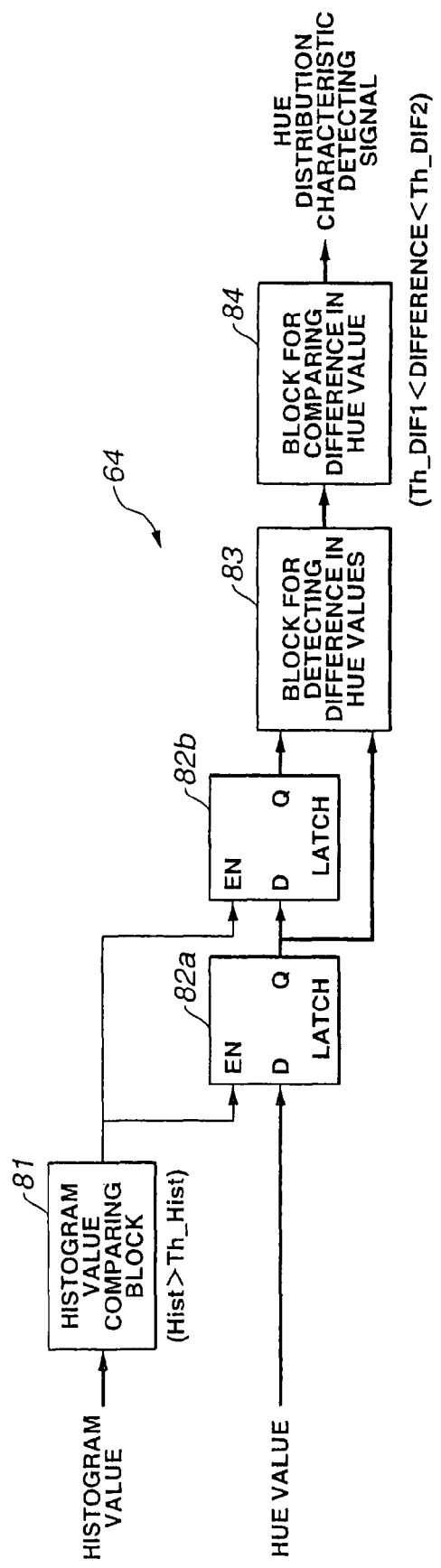

FIG. 18 shows the structure of hue distribution characteristic detecting block 64 in FIG. 13. The hue distribution characteristic detecting block 64 comprises: a histogram value comparing block 81 for comparing a histogram value Hist with a predetermined threshold value Th_Hist; latch circuits 82a and 82b for latching the corresponding hue values; and a block 83 for calculating the difference in hue values for calculating the difference between the latched hue values;

and a block 84 for comparing the difference in hue values for comparing whether or not the difference is within a predetermined range.

Figure 19A:
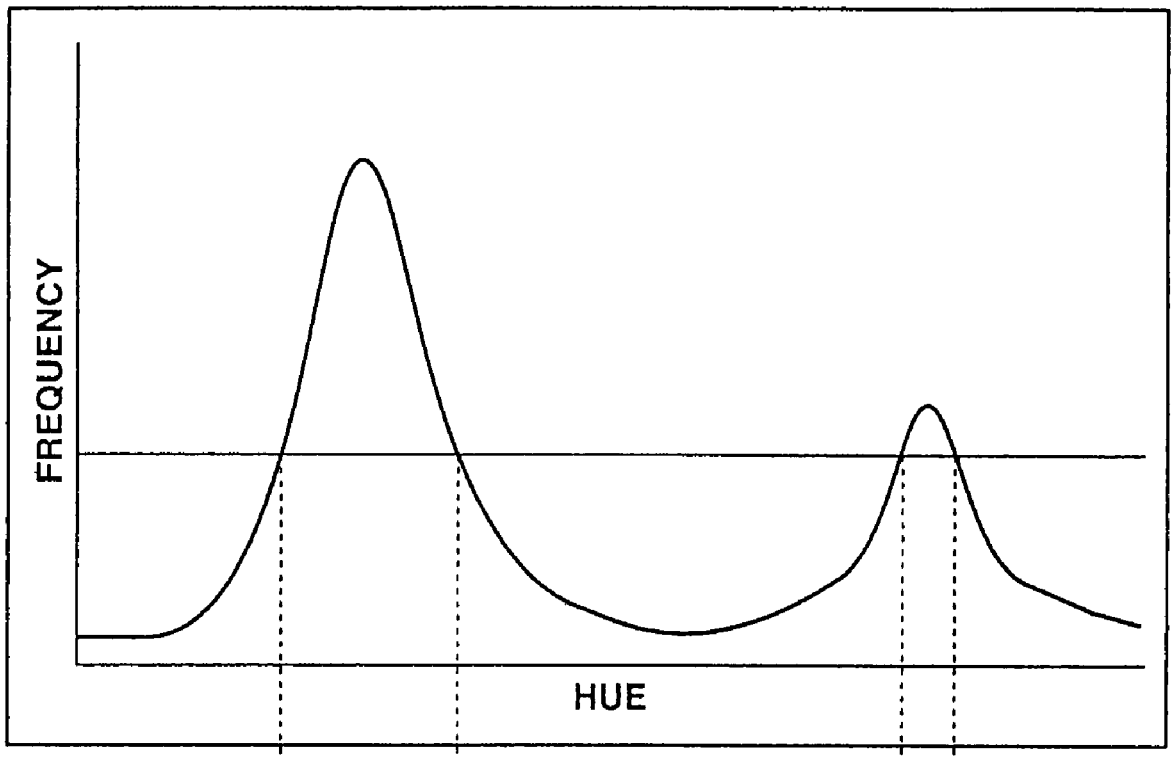
Figure 19B:
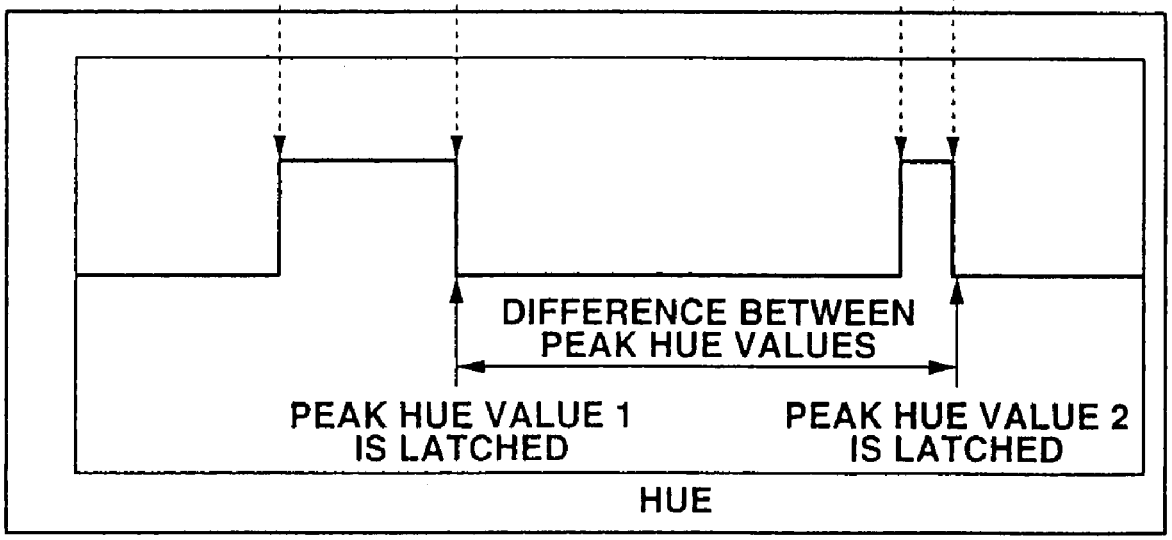

A description is given of the operation of the hue distribution characteristic detecting block 64 with reference to FIGS. 19A and 19B.

FIG. 19A shows the histogram of the inputted hue values. FIG. 19B shows an explanatory diagram of the operation for comparing the histogram value of the hue value with the threshold value and for detecting the distance between the hue values.

As mentioned above, the histogram value comparing block 81 compares the histogram value of the hue value with the threshold value, thereby outputting the pulses near the position of the peak value of the histogram. The latch circuits 82a and 82b shown in FIG. 18 latch the corresponding hue values by the pulses. The block 83 for calculating the difference in hue values at the next stage calculates the distance between the hue values by using the latched hue values.

That is, as shown in FIG. 19B, the distance between the peak hue values is obtained. When the distance is within a predetermined range (referring to FIG. 18, Th_DIF1<difference<Th_DIF2), the image has a portion with the hue different from that of the normal image and the block 84 for comparing the difference in hue values outputs a signal for detecting the characteristic of the hue distribution.

The saturation distribution characteristic detecting block 65 shown in FIG. 13 has the similar structure.

According to the first embodiment, the predetermined characteristic amount such as the number of pixels having the specific color in the image is detected based on the picked-up image. It is determined whether or not the detecting result is valid. Thus, the ratio for transmitting the picked-up image to the extra-corporeal unit 4 is controlled and it is possible to set, to the proper state, the power consumption for transmitting the image with the large load by the battery 21.

Further, according to the first embodiment, it is possible to efficiently obtain the necessary image on the extra-corporeal unit 4 side. It is advantageous to eliminate or extremely reduce the troublesome operation for extracting the necessary image from the unneeded images according to the conventional art.

That is, it is possible to reduce the unnecessary power consumption for transmitting the image upon picking up the invalid image. The detailed image for diagnosis can be transmitted to the extra-corporeal unit 4 without suppressing the image transmitting ratio upon picking up the valid image. Further, the electric energy of the battery 21 can effectively be used and the image for diagnosis can effectively be collected.

When the color of affected part is varied depending on the individual difference, the affected part such as changed color and hemorrhage is accurately detected without transmitting the unnecessary image. The detailed image for diagnosis is transmitted and the image diagnostic environment of the operator can be improved.

Second Embodiment

The second embodiment of the present invention will be described with reference to FIGS. 20 to 25.

FIG. 20 shows the structure of the processing block 15 according to the second embodiment. The image data inputted to the processing block 15 is inputted to an image size reducing block 85, the invalid image detecting block 25, and the affected part detecting block 26.

The image size reducing block 85 controls the reduction of image size under the control of the invalid image detecting block 25 and the affected part detecting block 26.

That is, the image size reducing block 85 reduces the image size by the invalid image detecting signal from the invalid image detecting block 25 and suppresses the reduction of image size upon inputting the affected part detecting signal from the affected part detecting block 26.

The output image from the image size reducing block 85 is inputted to a compressing block 86. The compressing block 86 changes the compressing ratio by a control signal from the affected part detecting block 26 and outputs the compressed image to the communication block 17 shown in FIG. 2.

That is, the compressing block 86 reduces the compressing ratio of the image data and transmits, to the communication block 17, the compressed data which is compressed by the low compressing ratio upon inputting the affected part detecting signal from the affected part detecting block 26.

The communication block 17 transmits the compressed data to the extra-corporeal unit 4.

The invalid image detecting block 25 detects the invalid image (white compression, black compression, and non-change of obtained image). Further, the affected part detecting block 26 detects the absence or presence of the affected part or its similar part based on the image data.

The reducing ratio of image size and the compressing rate are controlled by a user control signal outputted from the control block 19 based on a command received from the extra-corporeal unit 4. Further, The on/off operation of the control is performed by the invalid image signal and the affected part detecting signal. As mentioned above, the compressing ratio of the image size is controlled by inputting the command from the user.

Figure 21:
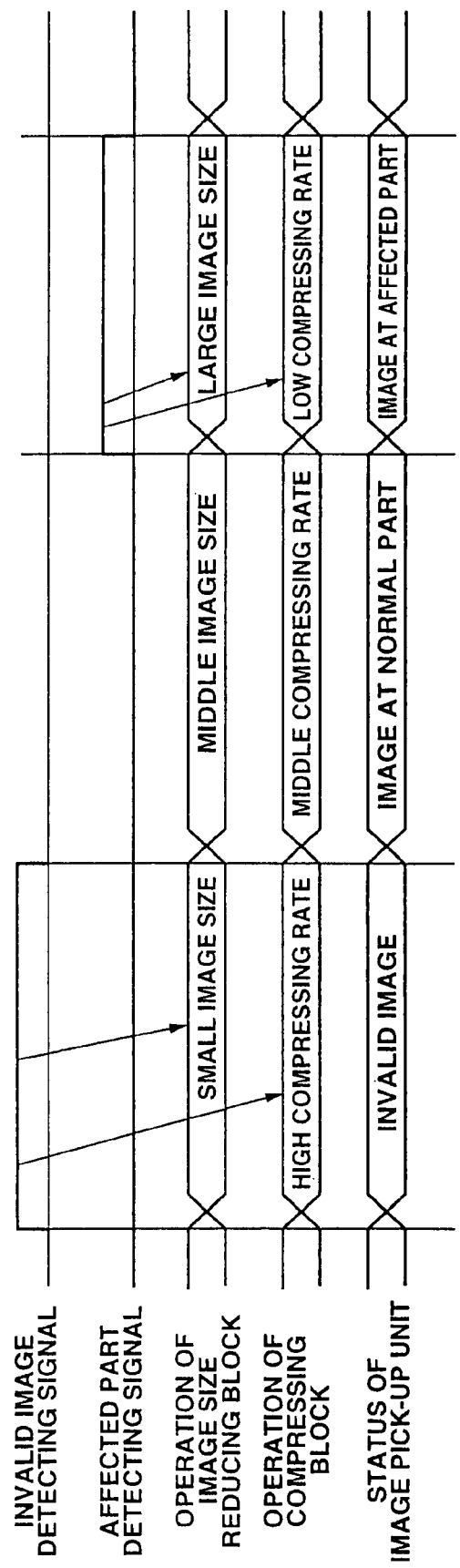
Figure 22:
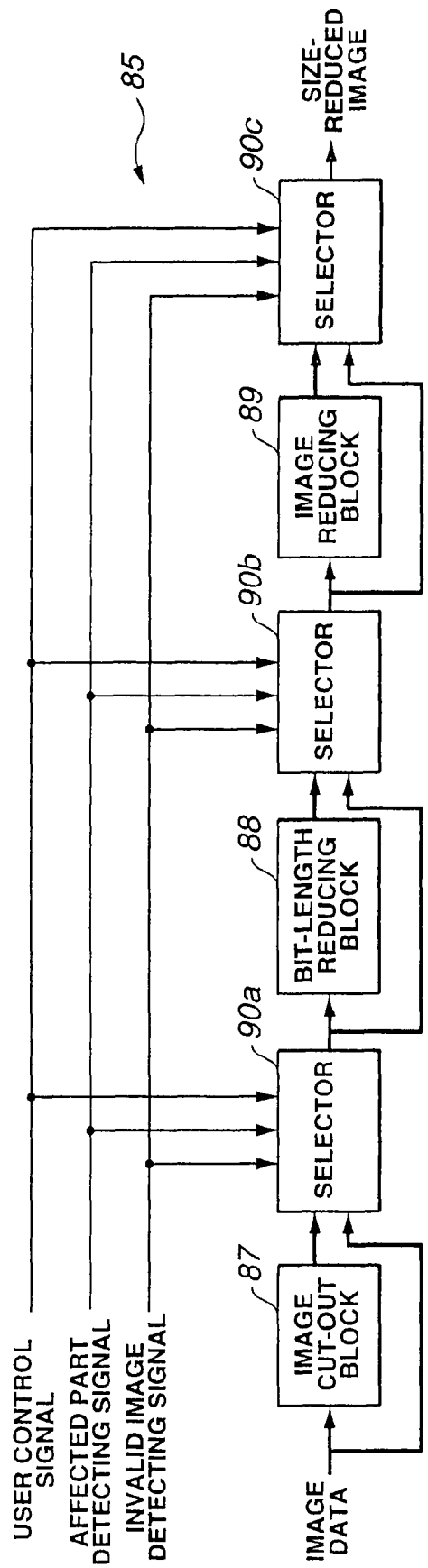

FIG. 21 shows a timing cart of the processing block 15.

Upon detecting the invalid image, the image size is minimized and the compressing ratio is maximized. Thus, the amount of transmitted data is suppressed to the minimum level. Because, mainly, information at the minimum level is transmitted to monitor the state of image pick-up unit 3.

Next, neither upon detecting the invalidity nor upon detecting the affected part, in other words, upon detecting the image at the normal part, the image size and the compressing ratio are set to the middle level. Because the image at the normal part for reference is transmitted to the extra-corporeal unit 4. When the affected part detection is active, the image size is not reduced because of increasing the amount of information of the affected-part image. Further, compressing ratio is reduced and the image is externally outputted with the highest quality.

The affected part detecting block 26 and the invalid image detecting block 25 shown in FIG. 20 have the same structures as those according to the first embodiment and therefore a description thereof is omitted.

FIG. 22A shows the structure of the image size reducing block 85 according to the second embodiment.

The image size reducing block 85 comprises: an image cut-out block 87; a Bit-length reducing block 88; an image reducing block 89; and selectors 90a, 90b, and 90c for selecting the image from the blocks. The image size reducing block 85 controls the operation such as the size reduction from the original image based on the affected part detecting signal, invalid image signal, and user control signal.

Referring to FIG. 22B, as the determining result of the invalid image signal and affected part detecting signal, specifically, depending on the cases of the invalid image, picking up the normal part, and detecting the affected part, the image whose size is reduced from the original image is outputted via the selectors 90a to 90c.

For example, the image cut-out block 87 reduces the number of pixels by decreasing an angle of view (pixel size of the image) by cutting out the image.

Figure 23:
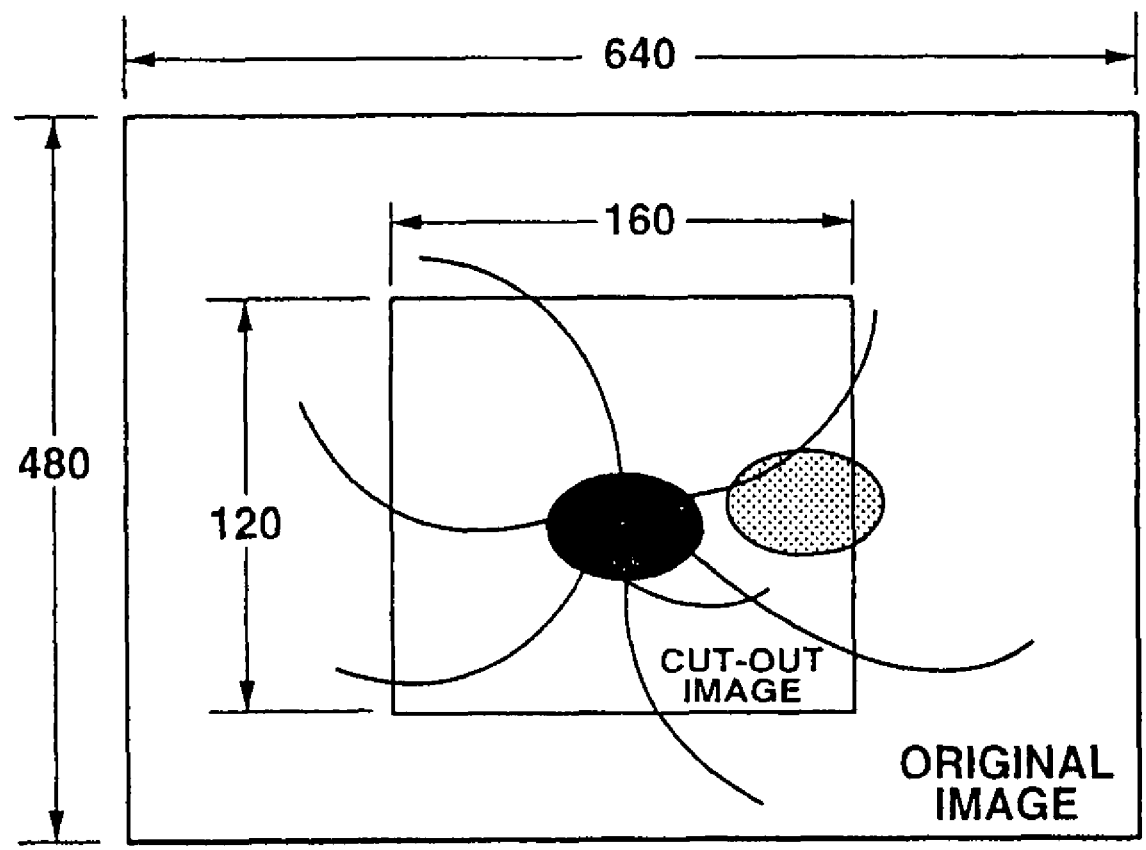

FIG. 23 shows an example of cutting out the image by the image cut-out block 87. In this example, only the center of the original image having (640×480) pixels is cut out. The center, specifically, the image having (160×120) pixels is outputted. Then, when the invalid image signal detects that the image is invalid, the cut-out image is outputted to the latter-stage side. When the invalid image signal does not detect that the image is invalid, the original image from which the image is not cut out is outputted to the latter-stage side.

The bit-length reducing block 88 shown in FIG. 22A reduces the image size by decreasing the bit length of the image.

According to the second embodiment, the gradation of 8 bits is reduced to that of 4 bits, thereby reducing the bit length of the image.

Figure 24:
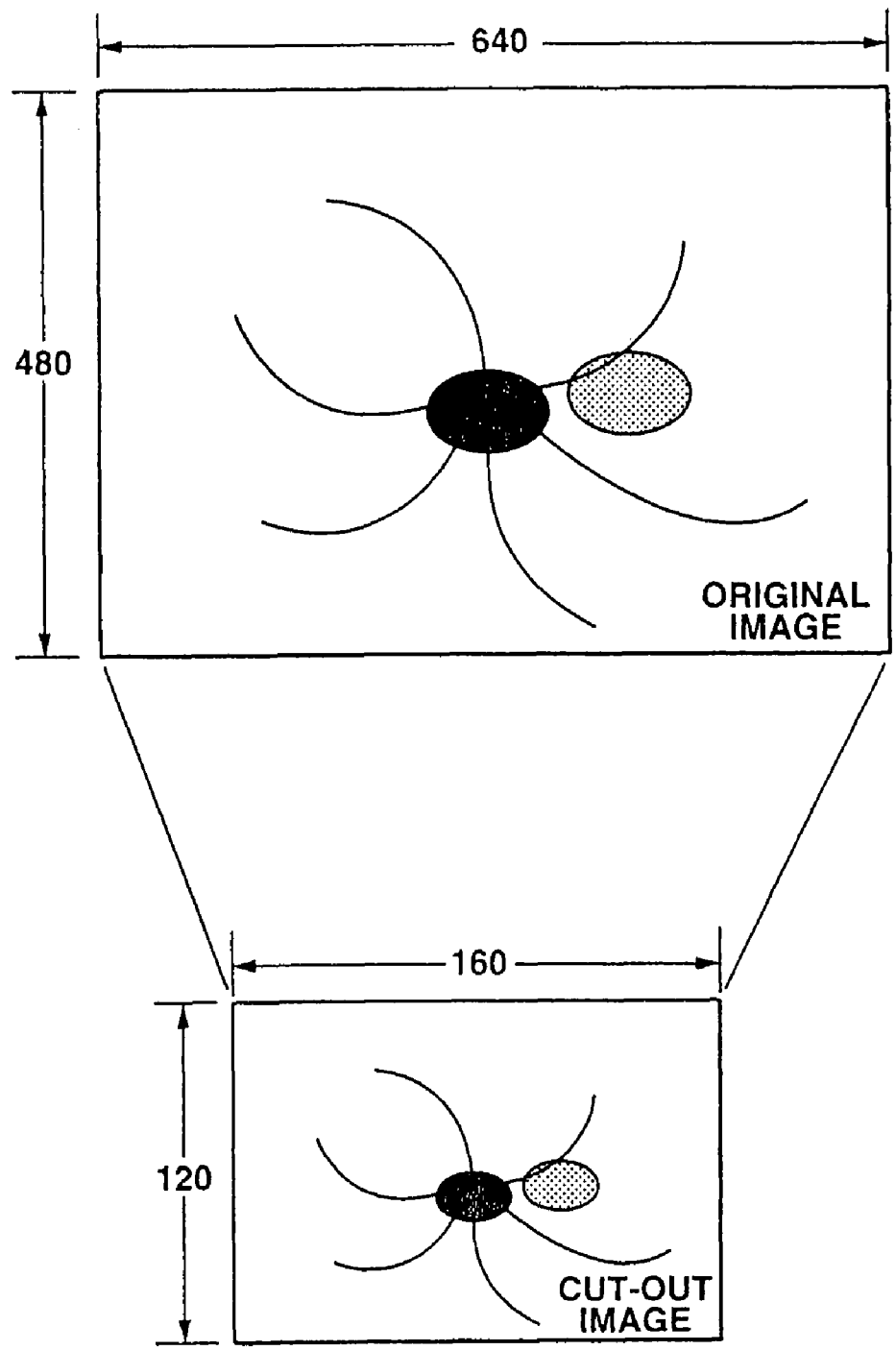

The image reducing block 89 thins out the pixels, and this example is shown in FIG. 24. In this example, the image having (640×480) pixels shown on the top side is reduced to the image having the (160×120) pixels by the thinning out the pixels as shown on the bottom side in FIG. 24. Since the simple thinning-out operation of pixels normally causes the problem on the image quality, the processing with the interpolation using the algorithm such as bi-linear and bi-cubic is performed.

According to the second embodiment, when it is determined that the image is invalid, the image is transmitted at the level for determining the state of the image pick-up unit 3, namely, the occurrence of white compression, black compression or stop. In this case, the image cut-out block cuts out the image of one part of the angle of view, and the Bit length is 4 bits by the Bit length reduction, thus to reduce the image.

Next, when neither the invalid image nor the affected part is detected, the image at the normal part is transmitted as the reference. Thus, the image cut-out operation and the reduction of Bit length stop and only the image is reduced, thus to output image.

Further, upon detecting the affected part, any image size is not reduced because of using the image for diagnosis with the highest image quality.

As mentioned above, it is possible to control the blocks by the user control signal which is transmitted by the command received from the extra-corporeal unit 4.

The compressing block 86 compresses the image data whose image size is reduced if necessary. According to the second embodiment, the image compression uses JPEG. In the case of the JPEG compression, the compressing ratio can arbitrarily be changed by a table of compressing parameters.

FIG. 25 shows the schematic structure of the compressing block 86 shown in FIG. 20. The compressing block 86 comprises: a high-compressing table 91, a middle-compressing compressing table 92, and a low-compressing table 93 which compress the data by high, middle, and low compressing ratios, respectively; a selector 94 for selecting one of the high-, middle-, and low-compressing tables 91 to 93; and a JPEG block 95 for JPEG-compressing the data by the selecting compressing table.

Upon inputting the invalid image detecting signal, the compressing table is switched to that with the high compressing ratio. Upon inputting the affected part detecting signal, the compressing table is switched to that with the low compressing ratio. Upon detecting neither the invalid image detecting signal nor the affected part detecting signal, the compressing table with middle compressing ratio is used.

Similarly to the image size reducing block, it is possible to control the tables by the user control signal which is transmitted by the command received from the extra-corporeal unit 4.

As mentioned above, according to the second embodiment, the image size and the compressed data size are switched depending on the determining result of the image importance (validity) and the compression and communication time is reduced. The consumption power is reduced and the image with high quality necessary for diagnosis can be transmitted.

The above control suppresses the power consumption of the battery 21 in the case of the unnecessary image and further enables the long use.

The present invention can variously be modified. According to the first and second embodiments, the transmitting interval of the image data and the size of transmitted data are independently controlled. However, the combination of the above two control operations can be used.

Further, other applications are considered, e.g., it is detected whether or not the area having the desired color has a predetermined size upon detecting the affected part and it is used by combining the above two control methods.

As mentioned above, according to the present invention, it is possible to control the amount of images transmitted to the extra-corporeal unit to the proper value without arranging the sensor in the image pick-up unit.

Having described the preferred embodiments of the invention referring to the accompanying drawings, it should be understood that the present invention is not limited to the those precise embodiments and various changes and modifications thereof could be made by one skilled in the art without departing from the spirit or scope of the invention as defined in the appended claims.

What is claimed is:

1. An endoscope image pick-up apparatus comprising:
an image pick-up unit for insertion into the body;
an extra-corporeal unit for receiving an image captured by the image pick-up unit by radio transmission, the extra-corporeal unit being arranged outside the body;
an image pick-up device for picking up an image in the body, the image pick-up device being provided in the image pick-up unit;
a storing device for storing the image picked up by the image pick-up device, the storing device being provided in the image pick-up unit; and
a processing device for reading the image from the storing device and performing a predetermined processing, the processing device being provided in the image pick-up unit,
wherein the storing device, when storing the image therein, operates at a high-speed clock same with that of an image pick-up operation by the image pick-up device, and when the processing device performs a predetermined processing to the image, operates at a low-speed clock same with that of the processing device.

2. The endoscope image pick-up apparatus according to claim 1, wherein the endoscope image pick-up apparatus comprises a clock selector serving as a clock switching device for switching between the high-speed clock and the low-speed clock.

3. The endoscope image pick-up apparatus according to claim 1, wherein the processing device performs a processing of compressing the image.

4. The endoscope image pick-up apparatus according to claim 1, wherein the processing device performs a processing of detecting a characteristic amount based on the image.

5. The endoscope image pick-up apparatus according to claim 1, wherein the image pick-up unit operates in a first time period and a second time period differing from each other, the first time period including operations by the image pick-up device of picking up the image and storing the picked up image into the storing device, and the second time period including operations by the processing device of reading the image from the storing device and performing the predetermined processing.

6. A method for radio transmission of images picked up by an image pick-up unit inserted into a body to an extra-corporeal unit arranged outside the body, the method comprising:

an image pick-up step of picking up an image in the body by an image pick-up device provided in the image pick-up unit;

a storage step of storing the image picked up by the, image pick-up device into a storing device, the storing device operates at a high-speed clock matched with that of an operation of the image pick-up device; and a processing step of reading the image from the storing device and performing a predetermined processing, by a processing device provided in the image pick-up unit, the storing device operates at a low-speed clock matched with that of the processing device.

7. The method of radio transmission of images according to claim 6, wherein the high-speed clock and the low-speed clock are switched by a clock selector.

8. The method of radio transmission of images according to claim 6, wherein the processing step compresses the image.

9. The method of radio transmission of images according to claim 6, wherein the processing step detects a characteristic amount based on the image.

10. The method of radio transmission of images according to claim 6, wherein the method operates in a first time period and a second time period differing from each other, the first time period including operations by the image pick-up device of picking up the image and storing the picked up image into the storing device, and the second time period including operations by the processing device of reading the image from the storing device and performing the predetermined processing.

* * * * *